United States Patent
Hale et al.

[11] Patent Number: 5,869,496
[45] Date of Patent: Feb. 9, 1999

[54] SPIRO-SUBSTITUTED AZACYCLES AS TACHYKININ RECEPTOR ANTAGONISTS

[75] Inventors: Jeffrey J. Hale, Westfield; Malcolm Maccoss, Freehold; Sander G. Mills, Woodbridge; Hongbo Qi, Edison; Shrenik K. Shah, Metuchen, all of N.J.

[73] Assignee: Merck & Co., Inc., Rahway, N.J.

[21] Appl. No.: 481,418

[22] PCT Filed: Jan. 25, 1994

[86] PCT No.: PCT/US94/00819

§ 371 Date: Jul. 11, 1995

§ 102(e) Date: Jul. 11, 1995

[87] PCT Pub. No.: WO94/17045

PCT Pub. Date: Aug. 4, 1994

[51] Int. Cl.$^6$ ..................... C07D 471/00; C07D 487/00; A61K 31/445

[52] U.S. Cl. .............. 514/278; 546/17; 546/18; 546/19

[58] Field of Search ................ 546/18, 17; 514/278

[56] References Cited

U.S. PATENT DOCUMENTS

| | | | |
|---|---|---|---|
| 4,420,485 | 12/1983 | Davis et al. | 514/278 |
| 5,091,387 | 2/1992 | Evans et al. | 514/278 |
| 5,219,860 | 6/1993 | Chambers et al. | 514/278 |

FOREIGN PATENT DOCUMENTS

| | | |
|---|---|---|
| 0 004 951 | 10/1979 | European Pat. Off. . |
| 0 004 952 | 10/1979 | European Pat. Off. . |
| 0 104 632 | 4/1984 | European Pat. Off. . |
| 0 139 138 | 5/1985 | European Pat. Off. . |
| 0 311 313 | 4/1989 | European Pat. Off. . |
| 0 428 434 A2 | 5/1991 | European Pat. Off. . |
| 0 431 943 A2 | 6/1991 | European Pat. Off. . |
| 0 445 974 | 9/1991 | European Pat. Off. . |
| 0 450 761 | 10/1991 | European Pat. Off. . |
| 0 474 561 A1 | 3/1992 | European Pat. Off. . |

OTHER PUBLICATIONS

Biochem and Biophys Res Comm vol. 184, No. 3, pp. 1418–1424 (May 15, 1992).
Life Sciences, vol. 50, No. 15, p. PL–101 Pl–106 (1992).
J. Pharmacol (1993) 108, 844–851, Y. Hirayama, et al.

*Primary Examiner*—Alan L. Rotman
*Attorney, Agent, or Firm*—David L. Rose; Richard C. Billups

[57] ABSTRACT

Disclosed are spiro-substituted azacycles of formula (I), are tachykinin receptor antagonists useful in the treatment of inflammatory diseases, pain or migraine, emesis and asthma. In particular compounds of formula (I) are shown to be neurokinin antagonists.

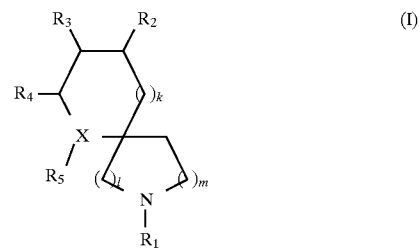

16 Claims, No Drawings

SPIRO-SUBSTITUTED AZACYCLES AS TACHYKININ RECEPTOR ANTAGONISTS

CROSS-REFERENCE

This application is a 371 of PCT/US 94/00819 filed Jan. 25, 1994.

BACKGROUND OF THE INVENTION

The invention disclosed herein is directed to certain spiro-substituted azacycles useful as tachykinin receptor antagonists. In particular, the compounds disclosed herein are neurokinin receptor antagonists.

The tachykinins, substance P (SP), neurokinin A (NKA) and neurokinin B (NKB), are structurally similar members of a family of neuropeptides. Each of these is an agonist of the receptor types, neurokinin-1 receptor NK-1), neuorokinin-2 receptor (NK-2) and neuorokinin-3 receptor (NK-3), which are so defined according to their relative abilities to bind tachykinins with high affinity and to be activated by the natural agonists SP, NKA and NKB respectively.

The tachykinins are distinguished by a conserved carboxyl-terminal sequence Phe-X-Gly-Leu-Met-$NH_2$. More specifically, substance P is a pharmacologically-active neuropeptide that is produced in mammals and possesses a characteristic amino acid sequence:

Arg-Pro-Lys-Pro-Gln-Gln-Phe-Phe-Gly-Leu-Met-$NH_2$

Neurokinin A possesses the following amino acid sequence:

His-Lys-Thr-Asp-Ser-Phe-Val-Gly-Leu-Met-$NH_2$.

Neurokinin B possesses the following amino acid sequence:

Asp-Met-His-Asp-Phe-Phe-Val-Gly-Leu-Met-$NH_2$.

(Chang et al., *Nature New Biol.* 232, 86 (1971); D. F. Veber et al., U.S. Pat. No. 4,680,283).

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.,* 1983, 35, 85–141). The NK1 and NK2 receptor subtypes are implicated in synaptic transmission (Laneuville et al., *Life Sci.,* 42: 1295–1305 (1988)).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science,* 199, 1359 (1978); P. Oehme et al. *Science,* 208, 305 (1980)) and plays a role in sensory transmission and pain perception (T. M. Jessell, *Advan. Biochem. Psychopharmacol.* 28, 189 (1981)). In particular, substance P has been shown to be involved in the transmission of pain in migraine (see B. E. B. Sandberg et al., *Journal of Medicinal Chemistry,* 25, 1009 (1982)), and in arthritis (Levine et al. *Science,* (1984) 226 547–549).

In the airways, it has been indicated that NK1 receptors are associated with microvascular leakage and mucus secretion, while NK2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al. *Life Sci.,* 49, 1941–1953 (1991); Advenier, et al., *Biochem. Biophys. Res. Comm.,* 184(3), 1418–1424 (1992)).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (Barnes P. J., *Lancet,* pp242–44 (1986); Rogers D. R., Aursudkij B., Barnes P. J., *Euro. J. Pharmacol,* 174, 283–86 (1989)).

Inhalation of bradykinin causes bronchoconstriction in asthmatic patients but not in normal subjects. (Fuller R. W., Dixon C. M. S., Cuss F. M. C., Barnes P. J., *Am Rev Respir Dis,* 135, 176–80 (1987)). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes bronchoconstriction in dogs. (Kaufman M. P., Coleridge H. M., Coleridge J. C. G., Baker D. G., *J. Appl. Physio.,* 48, 511–17 (1980)). In guinea-pig airways, bradykinin causes a bronchoconstrictor response by way of cholinergic and sensory-nerve-mediated mechanisms. (Ichinoe M., Belvisi M. G., Barnes P. J., *J. Pharmacol. Exp. Ther.,* 253, 594–99 (1990). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchocontriction in asthmatic patients. (Ichinoe, M. et al., *Lancet,* vol. 340, pp 1248–1251 (1992)).

The tachykinins have also been implicated in gastrointestinal (GI) disorders and diseases of the GI tract, such as inflammatory bowel disease, ulcerative colitis and Crohn's disease, etc. (see Mantyh et al., *Neuroscience,* 25 (3), 817–37 (1988) and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in *J. Rheumatol.* (1988) 15(12) 1807–10). Therefore, substance P is believed to be involved in the inflammatory response in diseases such as rheumatoid arthritis and osteoarthritis (O'Byrne et al., in Arthritis and Rheumatism (1990) 33 1023–8). Other disease areas where tachykinin antagonists are believed to be useful are allergic conditions (Hamelet et al., Can. J. Pharmacol. Physiol. (1988) 66 1361–7), immunoregulation (Lotz et al., Science (1988) 241 1218–21, Kimball et al., J. Immunol. (1988) 141 (10) 3564–9 and A. Perianin, et al., *Biochem. Biophys. Res. Commun.* 161, 520 (1989)) vasodilation, bronchospasm, reflex or neuronal control of the viscera (Mantyh et al., PNAS (1988) 85 3235–9) and, possibly by arresting or slowing β-amyloid-mediated neurodegenerative changes (Yankner et al., *Science,* (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster presented at C.I.N.P. XVIIIth Congress, 28th Jun.-2nd Jul., 1992]. Antagonists selective for the substance P and/or the neurokinin A receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992)). These antagonists may also be useful in the treatment of emesis. See C. Bountra, K. Bounce, T. Dale, C. Gardner, C. Jordan. D. Twissell and P. Ward, Eur. J. Pharnacol., 249, R3–R4 (1993) "Anti-emetic profile of a non-peptide neurokinin NK1 receptor antagonist, CP-99,994, in the ferret.

SUMMARY OF THE INVENTION

This invention is directed to compounds of formula I:

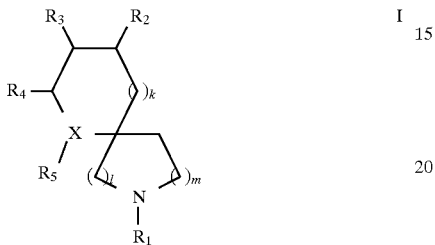

The invention is also concerned with pharmaceutical formulations with these novel compounds as active ingredients and the use of the novel compounds and their formulations in the treatment of certain disorders.

The compounds of this invention are tachykinin receptor antagonists and are useful in the treatment of inflammatory diseases, pain, migraine, asthma and emesis.

DETAILED DESCRIPTION OF THE INVENTION

This invention is directed to compounds of formula I:

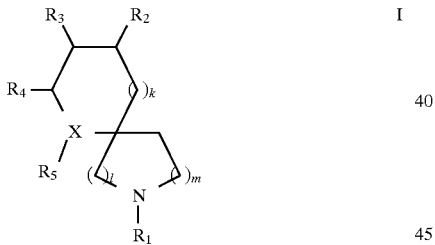

or a pharmaceutically acceptable salt thereof,
wherein the nitrogen expressly shown above is optionally quartenized with $C_{1-4}$alkyl or phenyl $C_{1-4}$alkyl or is optionally present as the N-oxide ($N^+O^-$), and wherein:

k is 0, 1 or 2;

l and m are each independently 0, 1, 2, 3, 4, or 5, with the proviso that l+m is equal to 1, 2, 3, 4, or 5;

$R_1$ is selected from a group consisting of:
(1) hydrogen,
(2) $C_{1-8}$ linear or branched alkyl, unsubstituted or mono, di, tri or tetra substituted, the substitutents independently selected from:
(a) hydroxy,
(b) oxo,
(c) cyano,
(d) halogen,
(e) trifluoromethyl,
(f) phenyl or naphthyl or mono, di or trisubstituted phenyl or naphthyl, the substitutents independently selected from 2(a) to 2(e) and 2(h) to 2(q) and phenyl;

(g) —$NR_6R_7$, wherein $R_6$ and $R_7$ are independently selected from:
(1) hydrogen,
(2) $C_{1-6}$ alkyl, or mono or disubstituted $C_{1-6}$ alkyl, the substitutents independently selected from 2(a) to 2(e) and 2(h) to 2(q) and phenyl,
(3) phenyl or mono di or trisubstituted phenyl, the substitutents independently selected from 2(a) to 2(e) and 2(h) to 2(q); or
$R_6$ and $R_7$ are joined together to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from 2(a) to 2(e) and 2(h) to 2(q) and phenyl;
(h) —$NR_6COR_7$, wherein $R_6$ and $R_7$ are as defined immediately above,
(i) —$NR_6CO_2R_7$, wherein $R_6$ and $R_7$ are as defined immediately above,
(j) —$NR_6CONHR_7$, wherein $R_6$ and $R_7$ are as defined immediately above,
(k) —$NHS(O)_jR_6$, wherein $R_6$ is as defined immediately above and j=1 or 2,
(l) —$CONR_6R_7$, wherein $R_6$ and $R_7$ are as defined immediately above,
(m) —$COR_6$, wherein $R_6$ is as defined immediately above,
(n) —$CO_2R_6$, wherein $R_6$ is as defined immediately above,
(o) —$OR_6$, wherein $R_6$ is as defined immediately above,
(p) —$S(O)_jR_6$, wherein $R_6$ is as defined immediately above and j=0,1, or 2;
(q) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl,
(21) triazolyl,
wherein the heteroaryl is unsubstituted or mono di or trisubstituted, the substituents independently selected from 2(a) to 2(e) and 2(h) to 2(p) and phenyl,
wherein the nitrogen of definitions 2(g) as defined above, and 3(g) and 4(g) as defined below is optionally quaternized with $C_{1-4}$ alkyl or phenyl $C_{1-4}$ alkyl or is optionally present as the N-oxide ($N^+O^-$);
(3) $C_{2-8}$ linear or branched alkenyl, unsubstituted or mono, di, tri or tetra substituted, the substitutents independently selected from:

(a) hydroxy,
(b) oxo,
(c) cyano,
(d) halogen,
(e) trifluoromethyl,
(f) phenyl, unsubstituted or mono or disubstituted, the substituents independently selected from 3(a) to 3(e) and 3(h) to 3(q) and phenyl;
(g) —$NR_6R_7$, wherein $R_6$ and $R_7$ are as defined immediately above,
(h) —$NR_6COR_7$, wherein $R_6$ and $R_7$ are as defined immediately above,
(i) —$NR_6CO_2R_7$, wherein $R_6$ and $R_7$ are as defined immediately above,
(j) —$NR_6CONHR_7$, wherein $R_6$ and $R_7$ are as defined immediately above,
(k) —$NHS(O)_jR_6$, wherein $R_6$ is as defined immediately above and j=1 or 2,
(l) —$CONR_6R_7$, wherein $R_6$ and $R_7$ are as defined immediately above,
(m) —$COR_6$, wherein $R_6$ is as defined immediately above,
(n) —$CO_2R_6$, wherein $R_6$ is as defined immediately above,
(o) —$OR_6$, wherein $R_6$ is as defined immediately above,
(p) —$S(O)_jR_6$, wherein $R_6$ is as defined immediately above and j=0,1, or 2;
(q) heteroaryl, wherein heteroaryl is selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (16) quinolyl,
  (17) tetrazolyl,
  (18) thiadiazolyl,
  (19) thiazolyl,
  (20) thienyl,
  (21) triazolyl,
wherein the heteroaryl is unsubstituted or mono or disubstituted, the substituents independently selected from 3(a) to 3(e) and 3(h) to 3(p) and phenyl;
  (4) $C_{2-8}$ alkynyl, unsubstituted or mono, di tri or tetra substituted, the substitutents independently selected from;
(a) hydroxy,
(b) oxo,
(c) cyano,
(d) halogen,
(e) trifluoromethyl,
(f) phenyl, unsubstituted or mono or disubstituted, the substituents independently selected from 4(a) to 4(e) and 4(h) to 4(q) and phenyl;
(g) —$NR_6R_7$, wherein $R_6$ and $R_7$ are as defined immediately above,
(h) —$NR_6COR_7$, wherein $R_6$ and $R_7$ are as defined immediately above,
(i) —$NR_6CO_2R_7$, wherein $R_6$ and $R_7$ are as defined above() p3 (j) —$NR_6CONHR_7$, wherein $R_6$ and $R_7$ are as defined immediately above,
(k) —$NHS(O)_jR_6$, wherein $R_6$ is as defined immediately above and j=1 or 2,
(l) —$CONR_6R_7$, wherein $R_6$ and $R_7$ are as defined immediately above,
(m) —$COR_6$, wherein $R_6$ is as defined immediately above,
(n) —$CO_2R_6$, wherein $R_6$ is as defined immediately above, p3 (o) —$OR_6$, wherein $R_6$ is as defined immediately above,
(p) —$S(O)_jR_6$, wherein $R_6$ is as defined immediately above and j=0,1, or 2;
(q) heteroaryl, wherein heteroaryl is selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (16) quinolyl,
  (17) tetrazolyl,
  (18) thiadiazolyl,
  (19) thiazolyl,
  (20) thienyl,
  (21) triazolyl,
and wherein the heteroaryl is unsubstituted mono or di substituted, the substitutents selected from 4(a) to 4(e) and 4(h) to 4(p) and phenyl;
X is carbon, and
$R^2$, $R^3$, $R^4$, and $R^5$ are independently selected from a group consisting of:
  (1) hydrogen;
  (2) hydroxy;
  (3) oxo; and
  (4) —$NR_6R_7$, as defined above, wherein the nitrogen is optionally quaternized with $C_{1-4}$alkyl or phenyl$C_{1-4}$alkyl or is present as the N-oxide, or
$R^2$ and $R^3$, or $R^3$ and $R^4$, together form a carbon-carbon bond, or
$R^2$ and $R^3$, or $R^3$ and $R^4$, or $R^4$ and $R^5$ are joined to form an aryl or heteroaryl ring selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) phenyl

(12) pyrazinyl,
(13) pyrazolyl,
(14) pyridyl,
(15) pyrimidyl,
(16) pyrrolyl,
(17) quinolyl,
(18) thiadiazolyl,
(19) thiazolyl,
(20) thienyl, and
(21) triazolyl, wherein the aryl or heteroaryl ring is unsubstituted or mono di or trisubstituted, the substitutents independently selected from:
  (a) $C_{1-6}$ linear or branched alkyl,
  (b) $C_{2-6}$ linear or branched alkenyl,
  (c) $C_{2-6}$ linear or branched alkynyl,
  (d) cyano,
  (e) halogen,
  (f) trifluoromethyl,
  (g) $C_{1-6}$ alkoxy,
  (f) —$NR_6R_7$,
  (g) —$NR_6COR_7$, wherein $R_6$ and $R_7$ are as defined immediately above,
  (h) —$NR_6CO_2R_7$, wherein $R_6$ and $R_7$ are as defined immediately above,
  (i) —$NR_6CONHR_7$, wherein $R_6$ and $R_7$ are as defined immediately above,
  (j) —$NS(O)_jR_6$, wherein $R_6$ is as defined immediately above and j=1 or 2,
  (k) —$CONR_6R_7$, wherein $R_6$ and $R_7$ are as defined immediately above,
  (l) —$COR_6$, wherein $R_6$ is as defined immediately above,
  (m) —$CO_2R_6$, wherein $R_6$ is as defined immediately above,
  (n) —$S(O)_jR_6$, wherein $R_6$ is defined as immediately above and j=0, 1, or 2; or $R^2$, $R^3$ and $R^4$ are defined as above, and X—$R^5$ is oxygen or S—$(O)_i$, where i=0, 1, or 2.

In an alternative embodiment, the invention encompasses compounds of formula I

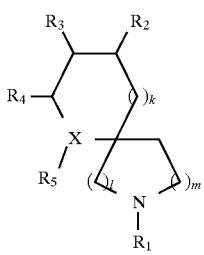

I or a pharmaceutically acceptable salts thereof wherein:
wherein the nitrogen expressly shown above is optionally quaternized with $C_{1-4}$alkyl or phenyl$C_{1-4}$alkyl or is optionally present as the N-oxide ($N^+O^-$), and wherein:
k is 0, 1 or 2;
l and m are each independently 0, 1, 2, 3, 4, or 5, with the proviso that l+m is equal to 1, 2, 3, 4, or 5;
$R_1$ is selected from a group consisting of:
  (1) hydrogen,
  (2) linear or branched $C_{1-8}$ alkyl, linear or branched $C_{2-8}$ alkenyl, or linear or branched $C_{2-8}$ alkynyl, wherein the $C_{1-8}$ alkyl, $C_{2-8}$ alkenyl or $C_{2-8}$ alkynyl is optionally mono, di, tri or tetra substituted, the substitutents independently selected from:
    (a) hydroxy,
    (b) oxo,
    (c) cyano,
    (d) halogen selected from Br, Cl, I, and F,
    (e) trifluoromethyl,
    (f) phenyl or mono, di or trisubstituted phenyl, the substitutents independently selected from
      (1) phenyl,
      (2) hydroxy,
      (3) $C_{1-3}$alkyl,
      (4) cyano,
      (5) halogen,
      (6) trifluoromethyl,
      (7) —$NR_6COR_7$, wherein $R_6$, $R_{6'}$ and $R_7$ are independently selected from:
        (a) hydrogen,
        (b) $C_{1-6}$ alkyl, or mono or disubstituted $C_{1-6}$ alkyl, the substitutents independently selected from
          (1) phenyl,
          (2) hydroxy,
          (3) oxo,
          (4) cyano,
          (5) halogen,
          (6) trifluoromethyl,
        (c) phenyl or naphthyl or mono di or trisubstituted phenyl or naphthyl, the substitutents independently selected from
          (1) hydroxy,
          (2) $C_{1-3}$alkyl,
          (3) cyano,
          (4) halogen,
          (5) trifluoromethyl,
          (d) $C_{1-3}$alkyloxy,
or
$R_6$ is defined as above and $R_6$ and $R_7$ are joined together with the nitrogen to which they are attached to form a 5-, 6-, or 7-membered monocyclic saturated ring containing 1 or 2 heteroatoms independently selected from nitrogen, oxygen, and sulfur, and in which the ring is unsubstituted or mono or disubstituted, the substituents independently selected from
  (a) hydroxy,
  (b) oxo,
  (c) cyano,
  (d) halogen,
  (e) trifluoromethyl,
      (8) —$NRCO_2R_7$,
      (9) —$NR_6CONHR_7$,
      (10) —$NR_6S(O)_jR_7$, wherein j is 1 or 2,
      (11) —$CONR_6R_7$,
      (12) —$COR_6$,
      (13) —$CO_2R_6$,
      (14) —$OR_6$,
      (15) —$S(O)_{k'}R_6$ wherein k' is 0, 1 or 2,
      (16) heteroaryl, wherein heteroaryl is selected from the group consisting of:
        (1) benzimidazolyl,
        (2) benzofuranyl,
        (3) benzooxazolyl,
        (4) furanyl,
        (5) imidazolyl,
        (6) indolyl,
        (7) isooxazolyl,
        (8) isothiazolyl,
        (9) oxadiazolyl,
        (10) oxazolyl,

(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl, and
(21) triazolyl,
wherein the heteroaryl is unsubstituted or mono di or trisubstituted, the substituents independently selected from,
(a) hydroxy,
(b) oxo,
(c) cyano,
(d) halogen,
(e) trifluoromethyl,
  (g) —$NR_6R_7$,
  (h) —$NR_6COR_7$,
  (i) —$NR_6CO_2R_7$,
  (j) —$NR_6CONHR_7$,
  (k) —$NR_6S(O)_jR_7$,
  (l) —$CONR_6R_7$,
  (m) —$COR_6$,
  (n) —$CO_2R_6$,
  (o) —$OR_6$,
  (p) —$S(O)_k'R_6$,
  (q) heteroaryl, wherein heteroaryl is selected from the group consisting of:
    (1) benzimidazolyl,
    (2) benzofuranyl,
    (3) benzoxazolyl,
    (4) furanyl,
    (5) imidazolyl,
    (6) indolyl,
    (7) isooxazolyl,
    (8) isothiazolyl,
    (9) oxadiazolyl,
    (10) oxazolyl,
    (11) pyrazinyl,
    (12) pyrazolyl,
    (13) pyridyl,
    (14) pyrimidyl,
    (15) pyrrolyl,
    (16) quinolyl,
    (17) tetrazolyl,
    (18) thiadiazolyl,
    (19) thiazolyl,
    (20) thienyl,
    (21) triazolyl,
  wherein the heteroaryl is unsubstituted or mono di or trisubstituted, the substituents independently selected from
    (1) phenyl,
    (2) hydroxy,
    (3) oxo,
    (4) cyano,
    (5) halogen,
    (6) trifluoromethyl,
wherein the nitrogen of definition $R_1$ 2(g) as defined above is optionally quaternized with $C_{1-4}$alkyl or phenyl$C_{1-4}$alkyl or is optionally present as the N-oxide ($N^+O^-$);
X is carbon, and
$R^2$, $R^3$, $R^4$, and $R^5$ are independently selected from a group consisting of:

(1) hydrogen;
(2) hydroxy;
(3) oxo; and
(4) —$NR_6R_7$ or —$NR_6C(O)$—$NR_6'R_7$, wherein the nitrogen of —$NR_6R_7$ is optionally quaternized with $C_{1-4}$alkyl or phenyl$C_{1-4}$alkyl or is optionally present as the N-oxide, or $R^2$ and $R^3$, or $R^3$ and $R^4$, together form a carbon-carbon bond, or
  $R^2$ and $R^3$, or $R^3$ and $R^4$, or $R^4$ and $R^5$ are joined to form an aryl or heteroaryl ring selected from the group consisting of:
    (1) benzimidazolyl,
    (2) benzofuranyl,
    (3) benzooxazolyl,
    (4) furanyl,
    (5) imidazolyl,
    (6) indolyl,
    (7) isooxazolyl,
    (8) isothiazolyl,
    (9) oxadiazolyl,
    (10) oxazolyl,
    (11) phenyl
    (12) pyrazinyl,
    (13) pyrazolyl,
    (14) pyridyl,
    (15) pyrimidyl,
    (16) pyrrolyl,
    (17) quinolyl,
    (18) thiadiazolyl,
    (19) thiazolyl,
    (20) thienyl, and
    (21) triazolyl,
and wherein the aryl or heteroaryl group is unsubstituted, mono, di or tri substituted, the substitutents selected from:
  (a) hydrogen,
  (b) $C_{1-6}$ alkyl, branched or unbranched, unsubstituted or mono
or disubstituted, the substituents being selected from hydrogen and hydroxy,
  (c) hydroxy
  (d) oxo
  (e) $OR_6$, wherein $R_6$ is as defined immediately above,
  (f) halogen,
  (g) trifluoromethyl,
  (h) nitro,
  (i) cyano,
  (j) $NHR_6$,
  (k) $NR_6R_7$,
  (l) $NHCOR_6$,
  (m) $NR_6COR_7$,
  (n) $NHCO_2R_6$,
  (o) $NR_6CO_2R_7$,
  (p) $NHS(O)_jR_6$,
  (q) $NR_6S(O)_jR_7$,
  (r) $CONR_6R_7$,
  (s) $COR_6$,
  (t) $CO_2R_6$,
  (u) $S(O)_k'R_6$,
  (v) heteroaryl, wherein heteroaryl is selected from the group consisting of:
    (a) benzimidazolyl,
    (b) benzofuranyl,
    (c) benzooxazolyl, (d) furanyl,
(e) imidazolyl,
(f) indolyl,
(g) isooxazolyl,
(h) isothiazolyl,
(i) oxadiazolyl,
(j) oxazolyl,
(k) pyrazinyl,
(l) pyrazolyl,
(m) pyridyl,
(n) pyrimidyl,
(o) pyrrolyl,
(p) quinolyl,
(q) tetrazolyl,
(r) thiadiazolyl,
(s) thiazolyl,
(t) thienyl,
(u) triazolyl, and wherein the heteroaryl is unsubstituted mono or di substituted, the substitutents selected from (1) hydrogen,
(2) $C_{1-6}$ alkyl, branched or unbranched, unsubstituted or mono or disubstituted, the substituents being selected from hydrogen and hydroxy, (3) hydroxy
(4) oxo
(5) $OR_6$,
(7) trifluoromethyl,
(8) nitro,
(9) cyano,
(10) $NHR_6$,
(11) $NR_6R_7$,
(12) $NHCOR_6$,
(13) $NR_6COR_7$,
(14) $NHCO_2R_6$,
(15) $NR_6CO_2R_7$,
(16) $NHS(O)_jR_6$,
(17) $NR_6S(O)_jR_7$,
(18) $CONR_6R_7$,
(19) $COR_6$,
(20) $CO_2R_6$,
(21) $S(O)_k'R_6$, and
(22) phenyl;

or $R^2$, $R^3$ and $R^4$ are defined as above, and X—$R^5$ is oxygen or S—$(O)_i$,
where i=0, 1, or 2.

As is clear from the examples and schemes, the designation:

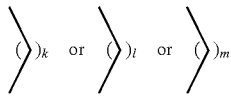

in formula I is interchangable with $(CH_2)_k$ or $(CH_2)_l$ or $(CH_2)_m$ respectively. As appreciated by those of skill in the art, halo as used herein are intended to include chloro, fluoro, bromo and iodo. Exemplfying the invention are the compounds of the examples including the group consisting of 1'-((3S)-(3,4-Dichlorophenyl)-4-(N-methyl) benzamidobutyl)spiro(1H-indene-1,4'-piperidine); 1'-((3S)-(3,4-Dichlorophenyl)-4-((N-methyl)-3,5-bis (trifluoromethyl)benzamidobutyl)spiro(1H-indene-1,4'-piperidine); 1'-((3S)-(3,4-Dichlorophenyl)-4-(N-methyl) benzamidobutyl)-3,4-dihydro-4-hydroxy-6-methoxy-spiro [2H-1-benzopyran-2,3'-piperidine]; 1'-((3S)-(3,4-Dichlorophenyl)-4-(N-methyl)benzamidobutyl)-3,4-dihydro-4-hydroxy-6-methoxy-spiro[2H-1-benzopyran-2, 4'-piperidine]; and 1'-((3S)-(3,4-Dichlorophenyl)-4-(N-methyl)benzamidobutyl)spiro(indane-1,4'-piperidine).

The compounds of the present invention are useful in the prevention and treatment of a wide variety of clinical conditions (as detailed in this specification) which are characterized by the presence of an excess of tachykinin, in particular substance P and NKA activity.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with an excess of tachykinins, especially substance P and NKA.

The compounds of the present invention are particularly useful in the treatment of pain or nociception and/or inflammation and disorders associated therewith such as, for example: neuropathy, such as diabetic or peripheral neuropathy and chemotherapy-induced neuropathy; asthma; osteoarthritis; rheumatoid arthritis; migraine and emesis.

For the treatment of any of these diseases compounds of Formula I may be administered orally, topically, parenterally, ICV, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.001 to 25 mg/kg per day, about 0.005 to 10 mg/kg per day, or about 0.005 to 5 mg/kg per day. Within this range the dosage may be 0.005 to 0.05, 0.05 to 0.5 or 0.5 to 5.0 mg/kg per day. The compounds may be administered on a regimen of 1 to 4 times per day, preferably once or twice per day.

Several methods for preparing the compounds of this invention are illustrated in the following Schemes and Examples.

The compounds of the present invention are prepared by alkylating azacycle I, in which $R_1$=H, under appropriate conditions (Scheme 1). The required azacycle starting materials are prepared using methods described in the literature; more specifically, as described in Claremon, D. A. et al, European Patent 0 431 943 943 A2, Evans, B. E. et al, U.S. Pat. No. 5,091,387, Davis, L. et al, U.S. Pat. No. 4,420,485, all of which are incorporated by reference, and Parham et al, *Journal of Organic Chemistry*, 41, 2628 (1976). None of the compounds in the foregoing references are alleged to be neurokinin antagonists.

Thus, azacycle I ($R_1$=H) is combined with the appropriate aldehyde and the intermediate imine is reduced to the tertiary amine chemically (e.g. using sodium cyanoborohydride) or catalytically (e.g. using hydrogen and palladium on carbon or Raney nickel catalyst) (Scheme 1). The aldehyde needed for this reaction can be prepared by methods generally known in the chemical literature; for the purposes of the present invention the preparation of a representative aldehyde is described in Hale, J. J.; Finke, P. E.; MacCoss, M. *Bioorganic and Medicinal Chemistry Letters*, 2, (February 1993).

In an alternative embodiment of the present invention, azacycle I ($R_1$=H) can be alkylated with an alkyl halide or alkyl sulfonate ester (with or without an added base to neutralize the mineral acid or sulfonic acid by-product) to give the desired compound (Scheme 1). The alkyl halide or alkyl sulfonate needed for this reaction can be prepared by methods generally known in the chemical literature; for the purposes of the present invention an aldehyde, prepared as described above, can be reduced to an alcohol with sodium borohydride, diisobutylaluminum hydride or lithium aluminum hydride, and the product alcohol converted to either the alkyl halide using methods described in March J. "Advanced Organic Chemistry", 3rd ed., John Wiley & Sons, New York, pp. 382–384 (1985), or alkyl sulfonate ester using methods described in March J. "Advanced Organic Chemistry", 3rd ed., John Wiley & Sons, New York, p. 444 (1985).

In an alternative embodiment of the present invention, I ($R_1$=H) can be acylated to give the tertiary amide and subsequent reduction with a strong reducing agent (e.g. diborane including borane dimethylsulfide; and, lithium aluminum hydride) will give the desired compound (Scheme 1). The acylating agent needed for this reaction can be prepared by methods generally known in the chemical literature; for the purposes of the present invention an aldehyde, prepared as described above, can be oxidized using such commonly used reagents as permanganate in acid or silver oxide, and the resulting acid activated as an acid chloride or mixed anhydride which can be used to acylate I ($R_1$=H). The product amide can in and of itself be a neurokinin antagonist or can be reduced with a strong reducing agent, such as diborane of lithium aluminum hydride, to give the tertiary amine.

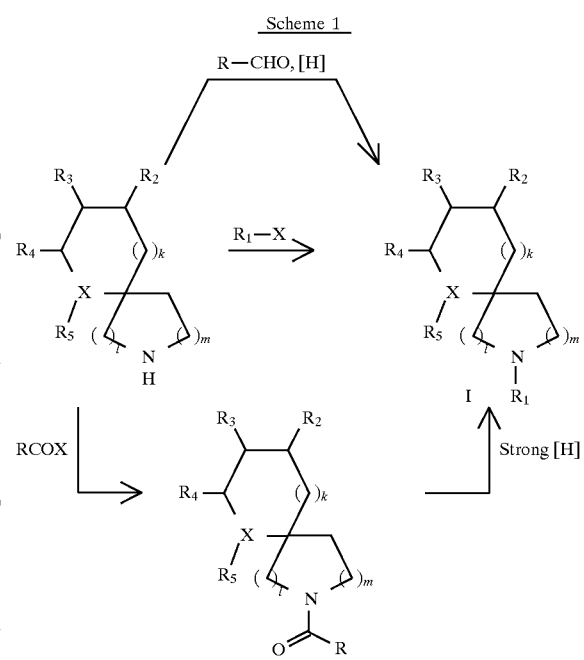

wherein $R_1$ as defined in this specification is R—$CH_2$.

EXAMPLE 1

1'-(3-(S)-(3,4-Dichlorophenyl)-4-(N-methyl)benzamidobutyl)spiro(1H-indene-1,4'-piperidine)

A mixture of 125 mg (0.36 mmol) of (3S)-(3,4-dichlorophenyl)-4-(N-methyl)benzamidobutanal, 107 mg (0.48 mmol) of spiro(1H-indene-1,4'-piperidine) hydrochloride, and 100 mg of activated 3 Å molecular sieves in 2 mL of methanol was treated with 1.5 mL of 1.0M sodium cyanoborohydride solution in THF and stirred at room temperature for 20 hours. The mixture was filtered through a pad of Celite; the reaction flask and filtered solids were rinsed well with methanol (~25 mL). Saturated sodium bicarbonate solution (5 mL) was added to the filtrate and the resulting milky mixture was concentrated in vacuo. The residue was partitioned between 25 mL of ethyl acetate and 10 mL of water and the layers were separated. The organic layer was dried over magnesium sulfate and concentrated in vacuo. Flash chromatography on 8 g of silica gel using ether, then 20:1 v/v ether/methanol as the eluant afforded 146 mg (78%) of the title compound as a foam.

$^1$H NMR (CDCl$_3$, 400 MHz, ppm, ranges are given due to amide rotamers and line broadening): δ 0.80–4.05 ppm (18H), 6.75 (app s, 1H), 6.79 (app s, 1H), 6.95–7.50 (12H).

2.69 and 3.04 (—CH$_2$N(CH$_3$)COPh)

Mass Spectrum (FAB): 521 (M+H, $^{37}$Cl+$^{35}$Cl isotope), 519 (M+H, $^{35}$Cl+$^{35}$Cl isotope).

The following table summarizes compounds that were prepared using a procedure analogous to EXAMPLE 1 substituting the required spiroazacycle hydrochloride for the spiro(1H-indene-1,4'-piperidine) hydrochloride. Methylene chloride/methanol/ammonium hydroxide (40:1:0.1 v/v/v) was used as the chromatography eluant.

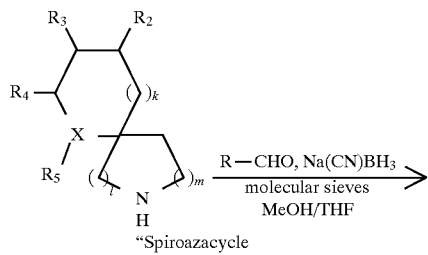
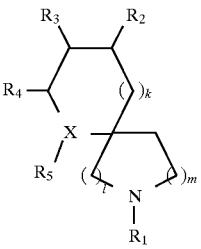
| EXAMPLE | "Spiroazacycle" | $R_1$ |
|---|---|---|
2 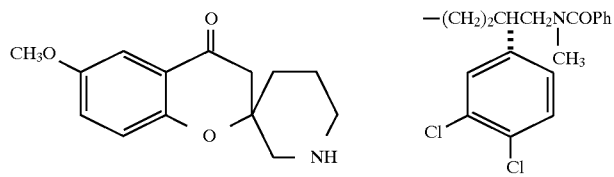
$^1$H NMR (CDCl$_3$, 400 MHz, ppm): δ 1.50–3.75 (20 H), 3.77 (s, 3 H), 6.62–7.43 (11 H).
Mass Spectrum (FAB): 583 (M + H, $^{37}$Cl + $^{35}$Cl isotope), 581 (M + H, $^{35}$Cl + $^{35}$Cl isotope).
3 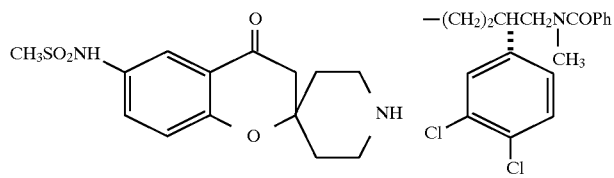
$^1$H NMR (CDCl$_3$, 400 MHz, ppm): δ 1.58–3.95 (24 H), 6.72–7.62 (11 H).
Mass Spectrum (FAB): 646 (M + H, $^{37}$Cl + $^{35}$Cl isotope), 644 (M + H, $^{35}$Cl + $^{35}$Cl isotope).
4 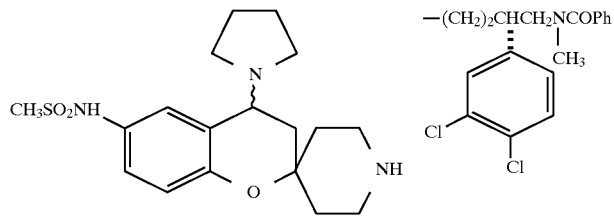
$^1$H NMR (CDCl$_3$, 400 MHz, ppm): δ 1.70–4.18 (33 H), 6.72–7.47 (11 H).
Mass Spectrum (FAB): 701 (M + H, $^{37}$Cl + $^{35}$Cl isotope), 699 (M + H, $^{35}$Cl + $^{35}$Cl isotope).
5 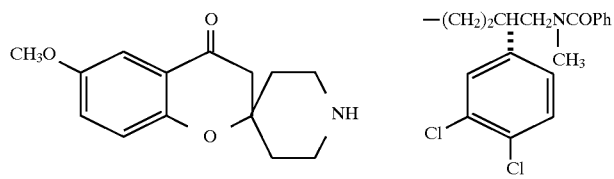
$^1$H NMR (CDCl$_3$, 400 MHz, ppm): δ 1.56–3.57 (20 H), 3.90 (m, 1 H), 6.72–7.43 (11 H).

-continued

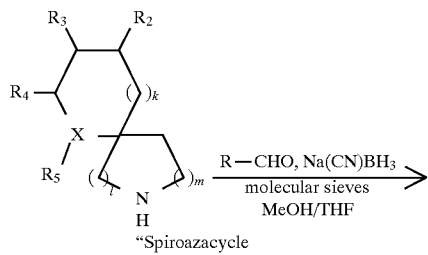
"Spiroazacycle"

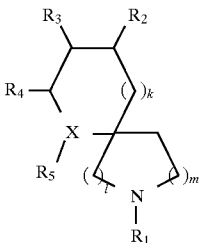

| EXAMPLE | "Spiroazacycle" | $R_1$ |
|---|---|---|

3.77 ($\underline{CH_3}O-$)
Mass Spectrum (FAB): 583 (M + H, $^{37}Cl + ^{35}Cl$ isotope), 581 (M + H, $^{35}Cl + ^{35}Cl$ isotope).

6 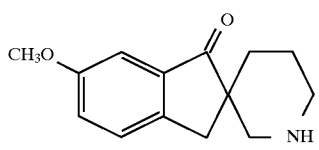 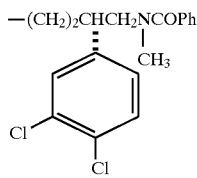

$^1$H NMR (CDCl$_3$, 400 MHz, ppm): δ 1.39–3.50 (20 H), 6.70–7.40 (11 H).
3.80 ($\underline{CH_3}O-$)
Mass Spectrum (FAB): 567 (M + H, $^{37}Cl + ^{35}Cl$ isotope), 565 (M + H, $^{35}Cl + ^{35}Cl$ isotope).

7 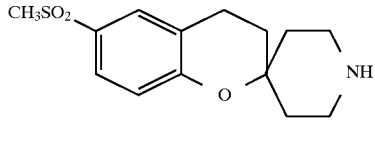 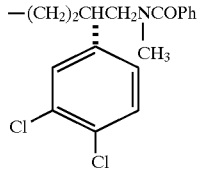

$^1$H NMR (CDCl$_3$, 400 MHz, ppm): δ 1.45–3.97 (25 H), 6.73–7.65 (11 H).
Mass Spectrum (FAB): 617 (M + H, $^{37}Cl + ^{35}Cl$ isotope), 615 (M + H, $^{35}Cl + ^{35}Cl$ isotope).

8 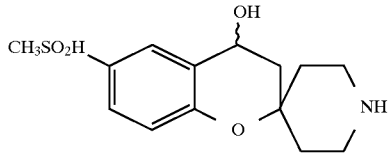 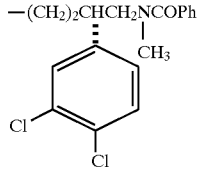

$^1$H NMR (CDCl$_3$, 400 MHz, ppm): δ 1.65–3.60 (24 H), 3.95 (m, 1 H), 4.75 (m, 1 H), 6.70–7.40 (11 H).
Mass Spectrum (FAB): 648 (M + H, $^{37}Cl + ^{35}Cl$ isotope), 646 (M + H, $^{35}Cl + ^{35}Cl$ isotope).

9 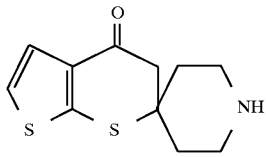 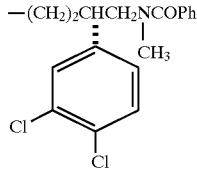

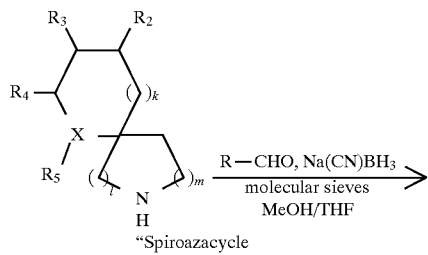

"Spiroazacycle"

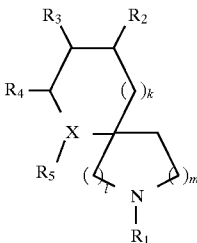

| EXAMPLE | "Spiroazacycle" | R₁ |
|---|---|---|
| | ¹H NMR (CDCl₃, 400 MHz, ppm): δ 1.40–3.95 (16 H), 6.70–7.45 (8 H), 7.00 (app s, 1 H), 7.03 (app s, 1 H). 2.67 and 2.81 ($-CH_2N(\underline{CH_3})COPh$) Mass Spectrum (FAB): 575 (M + H, ³⁷Cl + ³⁵Cl isotope), 573 (M + H, ³⁵Cl + ³⁵Cl isotope). | |
| 10 | 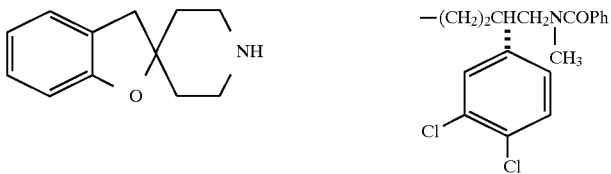 | $-(CH_2)_2CHCH_2NCOPh$ with $CH_3$, 3,4-dichlorophenyl |
| | ¹H NMR (CDCl₃, 400 MHz, ppm): δ 1.45–3.95 (17 H), 6.70–7.45 (12 H) 2.69 and 2.97 ($-CH_2N(\underline{CH_3})COPh$) Mass Spectrum (FAB): 525 (M + H, ³⁷Cl + ³⁵Cl isotope), 523 (M + H, ³⁵Cl + ³⁵Cl isotope). | |
| 11 | 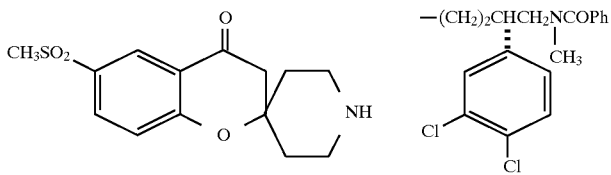 | $-(CH_2)_2CHCH_2NCOPh$ with $CH_3$, 3,4-dichlorophenyl |
| | ¹H NMR (CDCl₃, 400 MHz, ppm): δ 1.60–3.95 (23 H), 6.70–7.42 (9 H), 7.98 (dd, 1 H, J = 2.4, 8.7), 8.41 (d, 1 H, J = 2.32). Mass Spectrum (FAB): 631 (M + H, ³⁷Cl + ³⁵Cl isotope), 629 (M + H, ³⁵Cl + ³⁵Cl isotope). | |
| 12 | 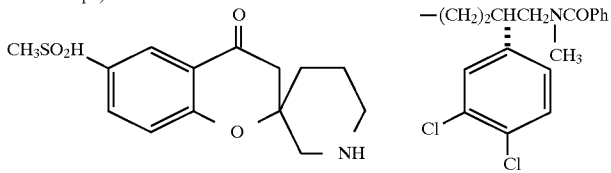 | $-(CH_2)_2CHCH_2NCOPh$ with $CH_3$, 3,4-dichlorophenyl |
| | ¹H NMR (CDCl₃, 400 MHz, ppm): δ 1.15–4.00 (24 H), 6.65–7.77 (11 H). Mass Spectrum (FAB): 645 (M + H, ³⁷Cl + ³⁵Cl isotope), 643 (M + H, ³⁵Cl + ³⁵Cl isotope). | |

EXAMPLE 13

1'-(3-(S)-(3,4-Dichlorophenyl)-4-((N-methyl)-3,5-bis (trifluoromethyl)benzamidobutyl)spiro(1H-indene-1,4'-piperidine)

STEP 1: N-Methyl-N-((2S)-(3,4-dichlorophenyl)-4-pentenyl)-3,5-bis(trifluoromethyl)benzamide A rapidly stirred mixture of 135 mg (0.55 mmol) of N-methyl (2S)-(3,4-dichlorophenyl)-4-pentenamine, 2 mL of saturated aqueous sodium bicarbonate solution and 4 mL of toluene was treated with 0.35 mL (1.9 mmol) of 3,5-bis (trifluoromethyl) benzoyl chloride and the resulting mixture was stirred at room temperature for 20 minutes. The reaction mixture was diluted with 25 mL of ether and the layers were separated. The organic layer was washed with 10 mL of 2.0N sodium hydroxide solution, 10 mL of 2.0N hydrochloric acid solution, 10 mL of saturated aqueous sodium chloride solution, dried over magnesium sulfate and concentrated in vacuo. Flash chromatography on 12 g of silica gel using 4:1 v/v hexanes/ether as the eluant afforded 263 mg (99%) of the title compound as an oil, $[\alpha]_D$=−27.6 (c=0.5, $CHCl_3$, 20° C.).

$^1$H NMR ($CDCl_3$, 400 MHz, ppm, ranges are given due to amide rotamers and line broadening): δ 2.15–3.85 (5H), 2.71 and 3.07 (3H, —$CH_2N(\underline{CH}_3)COAr$), 4.95–5.07 (2H, —$CH_2CH=\underline{CH}_2$), 5.40–5.75 (1H, —$CH_2=\underline{CH}_2$), 6.70–8.50 (6H).

IR (neat): 1726, 1643, 1470, 1371, 1228, 1122, 993, 905, 681.

Mass Spectrum (FAB): 486 ($^{37}Cl+^{35}Cl$ isotope), 484 ($^{35}Cl+^{35}Cl$ isotope).

Analysis: Calculated for $C_{21}H_{17}Cl_2F_6NO$ C, 52.08; H, 3.54; N, 2.89 Found: C, 51.13; H, 3.31; N, 2.45.

STEP 2: 1'-(3-(S)-(3,4-Dichlorophenyl)-4-((N-methyl)-3,5-bis(trifluoromethyl)benzamidobutyl)spiro(1H-indene-1,4'-piperidine).

A solution of 250 mg (0.52 mmol) of N-methyl-N-((2S)-(3,4-dichlorophenyl)-4-pentenyl)-3,5-bis(trifluoromethyl)benzamide (EXAMPLE 13, STEP 1) in 8 mL of 2:1:1 v/v/v acetone/t-butanol/water was treated with 5 mg (0.02 mmol) of osmium tetroxide. After 5 min, 91 mg (0.77 mmol) of N-methylmorpholine N-oxide was added and the resulting mixture was stirred at room temperature for 1.5 h. The reaction was quenched with approximately 100 mg of sodium bisulfite and concentrated in vacuo to 25% of the original volume. The residue was partitioned between 50 mL of methylene chloride and 20 mL of water and the layers were separated. The organic layer was dried over magnesium sulfate. The aqueous layer was extracted with 25 mL of methylene chloride; the extract was dried and combined with the original organic layer. The combined organic layers were concentrated in vacuo to afford the crude diol.

A solution of the diol in 8 mL of 3:1 v/v THF/water was treated with 197 mg (0.92 mmol) of sodium periodate. After 30 min, the reaction mixture was partitioned between 50 mL of ether and 25 mL of water and the layers were separated. The organic layer was dried. The aqueous layer was extracted with 50 mL of ether; the extract was dried and combined with the original organic layer. The combined organic layers were concentrated in vacuo. The residue was filtered through a pad of 10 g of silica gel using 3:2 v/v ether/hexanes as the eluant to afford 154 mg (61%) of aldehyde.

A solution of 150 mg (0.31 mmol) of aldehyde and 115 mg (0.52 mmol) of spiro(1H-indene-1,4'-piperidine) hydrochloride in 3 mL of methanol was treated with 1.5 mL of 1M sodium cyanoborohydride solution in THF. The mixture was stirred at rt for 16 h. The reaction was quenched with 5 mL of sat'd $NaHCO_3$ and the resulting mixture was partitioned between 30 mL of ether and 10 mL of water and the layers were separated. The organic layer was dried. The aqueous layer was extracted with 30 mL of ether; the extract was dried and combined with the original organic layer. The combined organic layers were concentrated in vacuo. Flash chromatography on 10 g of silica gel using 100:1 v/v, then 40:1 v/v $CH_2Cl_2$/methanol as the eluant afforded 134 mg (66% from the intermediate aldehyde) of the title compound as a foam.

$^1$H NMR ($CDCl_3$, 400 MHz, ppm, ranges are given due to amide rotamers and line broadening): δ 1.30–3.90 (15H), 6.73–6.80 (m, 2H), 7.05–7.90 (10H).

2.72 and 3.12 (—$CH_2N(\underline{CH}_3)COAr$)

Mass Spectrum (FAB): 656 ($^{37}Cl+^{35}Cl$ isotope), 654 ($^{35}Cl+^{35}Cl$ isotope).

Analysis: Calculated for $C_{33}H_{30}Cl_2F_6N_2O$ C, 60.47; H, 4.61; N, 4.27 Found: C, 59.84; H, 4.46; N, 3.97.

EXAMPLE 14

1'-((3S)-(3,4-Dichlorophenyl)-4-(N-methyl) benzamidobutyl)-3,4-dihydro-4-hydroxy-6-methoxy-spiro[2H-1-benzopyran-2,3'-piperidine]

A solution of 51 mg (0.088 mmol) of 1'-((3S)-(3,4-dichlorophenyl)-4-(N-methyl)benzamidobutyl)-3,4-dihydro-4-oxo-6-methoxy-spiro[2H-1-benzopyran-2,3'-piperidine] (EXAMPLE 2) in 1 mL of methanol at 0° C. was treated with 10 mg of sodium borohydride. The resulting mixture was warmed to room temperature and stirred for 30 minutes. The reaction was quenched with 1.0 mL of 2.0N sodium hydroxide solution and extracted with 3×10 mL of methylene chloride. The organic extracts were combined, dried over sodium sulfate and concentrated to afford 53 mg of the title compound.

$^1$H NMR ($CDCl_3$, 400 MHz, ppm, ranges are given due to amide rotamers and line broadening): δ 1.40–5.00 (25H), 6.70–7.42 (11H).

Mass Spectrum (FAB): 585 ($^{37}Cl+^{35}Cl$ isotope), 583 ($^{35}Cl+^{35}Cl$ isotope).

EXAMPLE 15

1'-((3S)-(3,4-Dichlorophenyl)-4-(N-methyl) benzamidobutyl)-3,4-dihydro-4-hydroxy-6-methoxy-spiro[2H-1-benzopyran-2,4'-piperidine]

The title compound was obtained from 1'-((3S)-(3,4-dichlorophenyl)-4-(N-methyl)benzamidobutyl)-3,4-dihydro-4-oxo-6-methoxy-spiro[2H-1-benzopyran-2,4'-piperidine] (EXAMPLE 5) using a procedure analogous to EXAMPLE 14.

$^1$H NMR ($CDCl_3$, 400 MHz, ppm, ranges are given due to amnide rotamers and line broadening): δ 1.40–3.58 (20H), 3.86 (m, 1H), 4.479 (br s, 1H), 6.70–7.41 (11H).

3.75 (3 H, $\underline{CH}_3O$—)

Mass Spectrum (FAB): 585 ($^{37}Cl+^{35}Cl$ isotope), 583 ($^{35}Cl+^{35}Cl$ isotope).

EXAMPLE 16

1'-((3S)-(3,4-Dichlorophenyl)-4-(N-methyl) benzamidobutyl)spiro(indane-1,4'-piperidine)

A mixture of 50 mg (0.096 mmol) of 1'-((3S)-(3,4-dichlorophenyl)-4-(N-methyl)benzamidobutyl)spiro(1H-indene-1,4'-piperidine) (EXAMPLE 1) and 7.5 mg 10% palladium on carbon catalyst in 2 mL of absolute ethanol was stirred under an atmosphere of hydrogen for 5 hours. The catalyst was filtered on a pad of Celite, the flask and filtered solids rinsed well with ethanol (20 mL) and the filtrate was concentrated in vacuo. Flash chromatography on 4 g of silica gel afforded 43 mg of the title compound as an oil.

$^1$H NMR ($CDCl_3$, 400 MHz, ppm, ranges are given due to amide rotamers and line broadening): δ 1.45–4.05 (22H), 6.80–7.60 (12H).

Mass Spectrum (FAB): 523 ($^{37}Cl+^{35}Cl$ isotope), 521 ($^{35}Cl+^{35}Cl$ isotope).

EXAMPLE 17

1'-(1-Oxo-(3S)-(3,4-dichlorophenyl)-4-(N-methyl) benzamidobutyl)spiro(1H-indene-1,4'-piperidine)

STEP 1: (3S)-(3,4-Dichlorophenyl)-4-(N-methyl) benzamidobutanal acid

A solution of 525 mg (1.5 mmol) of (3S)-(3,4-dichlorophenyl)-4-(N-methyl)benzamidobutanal in 10 mL of 1:1 v/v methanol 1.0N sodium hydroxide solution was treated with 463 mg (2.0 mmol) of freshly prepared silver oxide and the resulting mixture was stirred at room temperature for 20 hours. The reaction mixture was filtered through a pad of Celite and the flask and filtered solids were washed well with methanol (~25 mL). The filtrate was concentrated to ~10% of the original volume in vacuo and the residue was partitioned between 50 mL of ether and 50 mL of 2.0N hydrochloric acid solution and the layers were separated. The organic layer was washed with 25 mL of saturated aqueous sodium chloride solution, dried over magnesium sulfate and concentrated in vacuo. Flash chromatography on 30 g of silica gel using 1:1 v/v ethyl acetate/hexanes +1% acetic acid as the eluant afforded 540 mg (98%) of the title compound as a foam.

$^1$H NMR (CDCl$_3$, 400 MHz, ppm, ranges are given due to amide rotamers and line broadening): δ 1.20–4.00 (8H), 6.70–7.45 (8H).

Mass Spectrum (FAB): 368 ($^{37}$Cl+$^{35}$Cl isotope), 366 ($^{35}$Cl+$^{35}$Cl isotope).

STEP 2: 1'-(1-Oxo-(3S)-(3,4-dichlorophenyl)-4-(N-methyl)benzamidobutyl)spiro(1H-indene-1,4'-piperidine)

A solution of 315 mg (0.86 mmol) of (3S)-(3,4-dichlorophenyl)-4-(N-methyl)benzamidobutanoic acid (EXAMPLE 17, STEP 1) in 3 mL of methylene chloride was treated with 0.5 mL of oxalyl chloride and 1 drop of N,N-dimethylformamide. The resulting solution was stirred at room temperature for 20 minutes, then concentrated in vacuo. The residue was twice redissolved in 10 mL of ether and concentrated in vacuo.

A solution of the crude acid chloride in 5 mL of methylene chloride was slowly added to a solution of 300 mg (1.62 mmol) of spiro(1H-indene-1,4'-piperidine) and 0.52 mL (3.0 mmol) of N,N-diisopropylethyl amine in 5 mL of methylene chloride at 0° C. and the resulting solution was stirred cold for 1 hour. The reaction mixture was diluted with 40 mL of ethyl acetate and washed with 20 mL of 2.0N hydrochloric acid solution, 20 mL of saturated aqueous sodium bicarbonate solution, 20 mL of saturated sodium chloride solution, dried over magnesium sulfate and concentrated in vacuo. Flash chromatography on 25 g of silica gel using 7:3 v/v, then 1:1 v/v methylene chloride/ethyl acetate as the eluant afforded 302 mg (66%) of the title compound as a foam.

$^1$H NMR (CDCl$_3$, 400 MHz, ppm, ranges are given due to amide rotamers and line broadening): d 1.20–2.00 (5H), 2.40–4.70 (11H), 6.79 (app s, 2H), 6.85–7.55 (12H).

Mass Spectrum (FAB): 535 ($^{37}$Cl+$^{35}$Cl isotope), 533 ($^{35}$Cl+$^{35}$Cl isotope).

EXAMPLE 18

1'-((3S)-(3,4-Dichlorophenyl)-(4)-((N-methyl)benzamido)pentyl)spiro(1H-indene-1,4'-piperidine)

STEP 1: N-Methoxy-N-methyl-(2S)-(3,4-dichlorophenyl)-4-pentenamide

A mixture of 306 mg (1.25 mmol) of (2S)-(3,4-dichlorophenyl)-4-pentenoic acid and 202 mg (1.50 mmol) of 1-hydroxybenzotriazole hydrate in 10 mL of methylene chloride was cooled to 0° C. and treated with 287 mg (1.50 mmol) of 1-(3-dimethylaminopropyl)-3-ethylcarbodiimide. The cooling bath was removed and after 45 min. a solution of 365 mg (3.75 mmol) of N,O-dimethylhydroxylamine hydrochloride and 522 μl (3.75 mmol) of triethylamine in 10 mL of methylene chloride was added via cannula. The mixture was then stirred at 22° C. for 4 hours and then quenched with 10 mL of water and diluted with 8 mL of methylene chloride. The layers were separated and the aqueous layer was extracted with methylene chloride (2×10 mL). The combined organic layers were washed with 10 mL of brine, dried over anhydrous sodium sulfate, filtered, and concentrated in vacuo. Flash chromatography on 75 g of silica gel using 1:9 v/v ethyl acetate/ hexane as the eluant afforded 319 mg (89%) of the title compound as a clear oil.

$^1$H-NMR (400 MHz, CDCl$_3$) δ 2.40 (pentet, 1H), 2.75 (pentet, 1H), 3.13 (s, 3H), 3.52 (s, 3H), 3.99–4.01 (m, 1H), 4.96–5.05 (m, 2H), 5.63–5.70 (m, 1H), 7.15 (dd, 1H), 7.35 (d, 1H), 7.41 (d, 1H).

Mass Spectrum (FAB): m/z 290 (M+H, $^{37}$Cl+$^{35}$Cl isotope, 50%), 288 (M+H, $^{37}$Cl+$^{37}$Cl isotope, 100%).

STEP 2: (3S)-(3,4-dichlorophenyl)-5-hexen-2-one

A solution of 319 mg (1.11 mmoL) of N-methoxy-N-methyl-(2S)-(3,4-dichlorophenyl)-4-pentenamide (EXAMPLE 18, STEP 1) in 10 mL of dry tetrahydrofuran was cooled to –70° C. and treated with 1.0 mL (1.40 mmol) of methyllithium and stirred between –70° C. to –40° C. After 3 hours, the reaction was quenched with 5 mL of water, and diluted with 10 mL of ethyl acetate. The layers were separated and the organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 44 g of silica gel using 1:3 v/v ethyl acetate/ hexane as the eluant afforded 250 mg (93%) of the title compound as a clear oil.

$^1$H-NMR (400 MHz, CDCl$_3$) δ 2.07 (s, 3H), 2.36 (pentet, 1H), 2.72 (pentet, 1H), 3.64 (t, 1H), 4.95–5.01 (m, 2H), 5.55–5.65 (m, 1H), 7.03 (dd, 1H), 7.30 (d, 1H), 7.39 (d, 1H).

Mass Spectrum (FAB): m/z 245 (M+H, $^{37}$Cl+$^{35}$Cl isotope, 30%), 243 (M+H, $^{37}$Cl+$^{37}$Cl isotope, 50%), 155 (60%), 119 (100%).

STEP 3: N-Methyl-(3S)-(3,4-dichlorophenyl)-5-hexen-2-amine

A mixture of 102 mg (0.42 mmoL) of (3S)-(3,4-dichlorophenyl)-5-hexen-2-one (EXAMPLE 18, STEP 2), 170 mg (2.52 mmol) of methylamine hydrochloride, and 234 μl (1.68 mmol) of triethylamine in 4.0 mL of methanol was treated with 16 mg (0.25 mmol) of sodium cyanoborohydride and stirred at 22° C. for 20 hours. Saturated aqueous sodium bicarbonate solution (1.0 mL) was added and the resulting milky mixture was diluted with 5.0 mL of ethyl acetate and 5.0 mL of water. The layers were separated and the organic layer was washed with water (3×5 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 42 g of silica gel using 10:1 v/v ether/hexane as the eluant afforded 64 mg of the higher R$_f$ isomer (Isomer A) and 22 mg of a lower R$_f$ isomer (Isomer B) both as yellow oils.

$^1$H-NMR (400 MHz, CDCl$_3$); Isomer A: δ 1.04 (d, 3H), 2.29–2.35 (m, 4H), 2.50–2.68 (m, 3H), 4.86–4.95 (m, 2H), 5.48–5.56 (m, 1H), 7.01 (dd, 1H), 7.26 (d, 1H), 7.34 (d, 1H); Isomer B: d 0.86 (d, 3H), 2.32–2.50 (m, 4H), 2.51–2.53 (m, 1H), 2.68–2.73 (m, 2H), 4.88–4.98 (m, 2H), 5.54–5.61 (m, 1H), 6.97 (dd, 1H), 7.22 (d, 1H), 7.33 (d, 1H).

Mass Spectrum (Isomer A) (FAB): m/z 260 (M+H, $^{37}$Cl+$^{35}$Cl isotope, 70%), 258 (M+H, $^{35}$Cl+$^{35}$Cl isotope, 100%).

STEP 4: N-Methyl-N-((2)-((3S)-(3,4-dichlorophenyl))-5-hexenyl)benzamide.

A solution of 197 mg (0.76 mmol) of N-methyl (3S)-(3,4-dichlorophenyl)-5-hexen-2-amine (Isomer A)

(EXAMPLE 18, STEP 3) in 7.0 mL of dry methylene chloride was cooled to −70° C. and treated with 160 μl (1.14 mmol ) of triethylamine and 177 μl (1.53 mmol) of benzoyl chloride. The cooling bath was removed and the reaction was stirred at 22° C. for 20 hours. The reaction was quenched with 3.0 mL of water and diluted with 8.0 mL of methylene chloride. The layers were separated and the aqueous layer was extracted with methylene chloride (2×5 mL). The combined organic layers were washed with 10 mL of brine, dried over anhydrous sodium sulfate, filtered, and concentrated in vacuo. Flash chromatography on 43 g of silica gel using 1:3 v/v ethyl acetate/ hexane as the eluant afforded 261 mg (95%) of the title compound as a clear oil.

$^1$H-NMR (400 MHz, CDCl$_3$, ranges are given due to amide rotamers and line broadening) δ 1.38–5.55 (13H), 6.70–7.38 (9H).

Mass Spectrum (FAB): m/z 364 (M+H, $^{37}$Cl+$^{35}$Cl isotope, 100%), 362 (M+H, $^{35}$Cl+$^{35}$Cl isotope, 70%).

STEP 5: (3S)-(3,4-Dichlorophenyl)-(4)-(N-methyl) benzamidopentanal

A solution of 261 mg (0.72 mmol) of N-methyl-N-((2?)-((3S)-(3,4-dichlorophenyl))-5-hexenyl)benzamide (EXAMPLE 18, STEP 4) in 4.0 mL of 2:1:1 v/v/v acetone/t-butanol/water was treated with 1.8 mg (0.01 mmol) of osmium tetroxide. After 5 min., 128 mg (1.08 mmol) of N-methylmorpholine N-oxide was added and the resulting mixture was stirred at 22° C. for 2 hours. The reaction was quenched with 84 mg of sodium bisulfite and concentrated in vacuo to 25% of the original volume. The residue was partitioned between 10 mL of methylene chloride and 15 mL of water and the layers were separated. The aqueous layer was extracted with methylene chloride (2×5 mL). The combined organic layers were dried over anhydrous sodium sulfate, filtered, and concentrated in vacuo.

A solution of the crude diol in 6.0 mL of 3:1 v/v THF/water was treated with 194 mg (0.90 mmol) of sodium periodate. After 30 min., the reaction mixture was partitioned between 10 mL of ethyl ether and 10 mL of water and the layers were separated. The organic layer was washed with water (2×10 mL), dried over anhydrous sodium sulfate, filtered, and concentrated in vacuo. The residue was filtered through a pad of 76 g of silica gel using ethyl ether as the eluant to afford 183 mg (70%) of the title compound as an oil.

$^1$H-NMR (400 MHz, CDCl$_3$, ranges are given due to amide rotamers and line broadening) δ 1.33 (d, 3H), 2.55 (s, 3H), 2.81–2.89 (m, 3H), 3.30–3.50 (m, 2H), 4.90–5.10 (m, 1H), 6.79–7.41 (m, 9H), 9.50 (s, 1H), 9.65 (s, 1H).

Mass Spectrum (FAB): m/z 366 (M+H, $^{37}$Cl+$^{35}$Cl isotope, 45%), 364 (M+H, $^{37}$Cl+$^{37}$Cl isotope, 65%), 242 (58%), 162 (100%), 136 (52%), 105 (53%).

STEP 6:1'-((2)-((3S)-(3,4-Dichlorophenyl)-5-(N-methyl)benzamido)pentyl)spiro(1H-indene-1,4'-piperidine)

A mixture of 70 mg (0.19 mmol) of (3S)-(3,4-dichlorophenyl)-(4)-(N-methyl)benzamidopentanal (EXAMPLE 18, STEP 5), 62 mg (0.28 mmol) of spiro(1H-indene-1-4'-piperidine) hydrochloride in 3.0 mL of methanol was treated with 36 mg (0.58 mmol) of sodium cyanoborohydride and stirred at 22° C. for 20 hours. Saturated sodium bicarbonate solution (1.0 mL) was added and the resulting milky mixture was concentrated to 50% of its original volume. The residue was partitioned between 20 mL of ethyl acetate and 10 mL of water and the layers were separated. The organic layer was washed with water (3×10 mL). The aqueous layers were extracted with 10 mL of ethyl acetate. The combined organic layers were washed with 10 mL of saturated aqueous sodium chloride solution, dried over anhydrous sodium sulfate, filtered, and concentrated in vacuo. Flash chromatography on 43 g of silica gel using 5:95 v/v methanol/methylene chloride as the eluant afforded 83 mg (81%) of the title compound as a white foam.

$^1$H-NMR (400 MHz, CDCl$_3$, ranges are given due to amide rotamers and line broadening) δ 1.22–5.11 (20H), 6.68–7.42 (m, 15H).

Mass Spectrum (FAB): m/z 569 (M+H, $^{37}$Cl+$^{35}$Cl isotope, 70%), 567 (M+H, $^{35}$Cl+$^{35}$Cl isotope, 100%).

EXAMPLE 19

1'-((2)-((3S)-(3,4-Dichlorophenyl)-5-(N-methyl)benzamido)pentyl)spiro(1-indane-1,4'-piperidine)

The title compound was prepared from 1'-((2)-((3S)-(3,4-dichlorophenyl)-5-(N-methyl)benzamido)pentyl)spiro(1H-indene-1,4'-piperidine) (EXAMPLE 18) using a procedure identical to EXAMPLE 16.

$^1$H-NMR (400 MHz, CDCl$_3$, ranges are given due to amide rotamers and line broadening) δ 1.36–5.28 (24H), 6.77 (d, 2H), 7.04–7.40 (m, 13H).

Mass Spectrum (FAB): m/z 538 (M+H, $^{37}$Cl+$^{35}$Cl isotope, 70%), 536 (M+H, $^{35}$Cl+$^{35}$Cl isotope, 100%).

EXAMPLE 20

1'-((3S)-(3,4-Dichlorophenyl)-(4)-((N-methyl)benzamido)octyl)spiro(1H-indene-1,4'-piperidine)

The title compound was prepared in 6 steps from (2S)-(3,4-dichlorophenyl)-4-pentenoic acid using procedures identical to those in EXAMPLE 18, substituting butyllithium for methyllithium in EXAMPLE 18, STEP 2.

$^1$H-NMR (400 MHz, CDCl$_3$, ranges are given due to amide rotamers and line broadening) δ 0.92 (t, 3H), 1.20–3.00 (24H), 6.69–6.90 (m, 4H), 7.15–7.41 (m, 10H).

Mass Spectrum (FAB): m/z 578 (M+H, $^{37}$Cl+$^{35}$Cl isotope, 70%), 576 (M+H, $^{35}$Cl+$^{35}$Cl isotope, 100%).

EXAMPLE 21

1'-((4)-((3S)-(3,4-Dichlorophenyl)-1-(N-methyl)benzamido)octyl)spiro(1H-indene-1,4'-piperidine)

The title compound was prepared from 1'-((4)-((3S)-(3,4-dichlorophenyl)-1-(N-methyl)benzamido)octyl)spiro(1H-indene-1,4'-piperidine) (EXAMPLE 20) using a procedure identical to EXAMPLE 16.

$^1$H-NMR (400 MHz, CDCl$_3$, ranges are given due to amide rotamers and line broadening) δ 0.92 (t, 3H), 1.35–2.87 (27H), 6.75 (d, 2H), 7.12–7.40 (m, 10H).

Mass Spectrum (FAB): m/z 580 (M+H, $^{37}$Cl+$^{35}$Cl isotope, 70%), 578 (M+H, $^{35}$Cl+$^{35}$Cl isotope, 100%).

Employing standard acylation procedures on 1'-[3-((S)-(3,4-dichlorophenyl))-4-(methylamino)butyl]-spiro[1H-indene-1,4'-piperidine (for example, as in Example 13, Step 1, or Example 18, Step 1), the following compounds were prepared:

EXAMPLE 22

1'-((3S)-(3,4-Dichlorophenyl)-4-((N-methyl)thiophene-2-carboxamidobutyl)spiro[1H-indene-1,4'-piperidine]

Mass Spectrum (FAB): m/Z 140,197,227,229,383,525

EXAMPLE 23

1'-((3S)-(3,4-Dichlorophenyl)-4-((N-methyl)benzenesulfonamidobutyl)spiro[1H-indene-1,4'-piperidine]

Mass Spectrum (FAB): m/Z 140,197,227,229,383,555, 557

EXAMPLE 24

1'-((3S)-(3,4-Dichlorophenyl)-4-((N-methyl)furan-2-carboxamidobutyl)spiro[1H-indene-1,4'-piperidine]

Mass Spectrum (FAB): m/Z 140,197,227,229,383,509, 511

EXAMPLE 25

1'-((3S)-(3,4-Dichlorophenyl)-4-((N-methyl)phenoxycarboxamidobutyl)spiro[1H-indene-1,4'-piperidine]

Mass spectrum (FAB): m/Z 140,197,227,229,383,535, 538

EXAMPLE 26

1'-((3S)-(3,4-Dichlorophenyl)-4-((N-methyl)phenylaminocarboxamidobutyl)spiro[1H-indene-1,4'-piperidine]

Mass Spectrum (FAB): m/Z 140,197,227,229,383,534, 536

EXAMPLE 27

1'-((3S)-(3,4-Dichlorophenyl)-4-((N-methyl)pyridine-2-carboxamidobutyl)spiro[1H-indene-1,4'-piperidine]

Mass Spectrum (FAB): m/Z 140,197,227,229,383,520, 522

EXAMPLE 28

1'-((3S)-(3,4-Dichlorophenyl)-4-((N-methyl)pyridine-3-carboxamidobutyl)spiro[1H-indene-1,4'-piperidine]

Mass Spectrum (FAB): m/Z 140,197,227,229,383,520, 522

EXAMPLE 29

1'-((3S)-(3,4-Dichlorophenyl)-4-((N-methyl)pyridine-4-carboxamidobutyl)spiro[1H-indene-1,4'-piperidine]

Mass Spectrum (FAB): m/Z 140,197,227,229,383,520, 522

EXAMPLE 30

1'-((3S)-(3,4-Dichlorophenyl)-4-((N-methyl)benzothiophene-2-carboxamidobutyl)spiro[1H-indene-1,4'-piperidine]

Mass Spectrum (FAB): m/Z 197,227,229,383,575,577

EXAMPLE 31

1'-((3S)-(3,4-Dichlorophenyl)-4-((N-methyl)thiophene-2-acetamidobutyl)spiro[1H-indene-1,4'-piperidine]

Mass Spectrum (FAB): m/Z 141,197,227,229,383,539, 541

EXAMPLE 32

1'-((3S)-(3,4-Dichlorophenyl)-4-((N-methyl)thiophene-3-carboxamidobutyl)spiro[1H-indene-1,4'-piperidine]

Mass Spectrum (FAB): m/Z 141,197,227,229,383,525, 526

EXAMPLE 33

1'-((3S)-(3,4-Dichlorophenyl)-4-((N-methyl)-(3-methylthiophene-2-carboxamido)butyl)spiro[1H-indene-1,4'-piperidine]

Mass Spectrum (FAB): m/Z 197,227,229,383,539,541

EXAMPLE 34

1'-((3S)-(3,4-Dichlorophenyl)-4-((N-methyl)-(5-methylthiophene-2-carboxamido)butyl)spiro[1H-indene-1,4'-piperidine]

Mass Spectrum (FAB): m/Z 141,197,227,229,383,539, 541

EXAMPLE 35

1'-((3S)-(3,4-Dichlorophenyl)-4-((N-methyl)-(5-chlorothiophene-2-carboxamido)butyl)spiro[1H-indene-1,4'-piperidine]

Mass Spectrum (FAB): m/Z 197,227,229,383,559,561 (cluster)

EXAMPLE 36

1'-((3S)-(3,4-Dichlorophenyl)-4-((N-methyl)-(2,3-dibromothiophene-5-carboxamido)butyl)spiro[1H-indene-1,4'-piperidine]

Mass Spectrum (FAB): m/Z 140,197,227,229,383,682 (cluster)

EXAMPLE 37

3-(S)-(3,4-Dichlorophenyl)-4-((t-butoxycarbonyl)methylamino)butanal

A solution of 10 g (41 mmol) of 3-(S)-(3,4-dichlorophenyl)-4-methylamino-1-pentene in 100 mL of CH2Cl2 was cooled in ice bath and treated with 5.8 mL (41 mmol) of triethylamine (Et3N) and 9 g (41 mmol) of di-t-butyl dicarbonate. The cold bath was removed after 5 min and the stirring was continued for 1 h. The reaction mixture was diluted with CH2Cl2 and washed with water, 1.2N HCl, saturated NaHCO3 and brine. The solution was dried over Na2SO4 and concentrated to give 14.58 g of residual oil.

$^1$H NMR (CDCl$_3$, ppm ranges are given because of amide rotomers and line broadening) δ 1.36 (s, 9H), 2.33 (m, 2H), 2.60 & 2.70 (2s, 3H), 2.8–3.6 (m, 3H), 4.94 (m, 2H), 5.59 (m, 1H), 6.9–7.4 (m, 3H).

The residue was dissolved in 80 mL of acetone, 40 mL of t-butanol and 40 mL of water. To this solution 1 mL of Osmium tetroxide (4% solution in water) and 5.15 g (44 mmol) of 4-methylmorpholine N-oxide were added. After stirring for 26 h, the reaction was quenched with approximately 5 g of Na2SO3 and concentrated to 25% of the original volume. The residue was partitioned between water and 1:1 ether (Et2O), ethyl acetate (EtOAc), the layers were separated and the aqueous layer was extracted with Et2O:EtOAc. Each organic layer was washed with water, brine and dried by filtering through Na2SO4. The filtrate was concentrated to afford the crude diol.

A solution of the diol in 120 mL of tetrahydrofuran (THF) and 40 mL of water was treated with 9.42 g (44 mmol) of sodium periodate. After stirring for 2 h, the reaction was diluted with Et2O:EtOAC and washed with water and brine.

The organic layer was dried (Na2SO4) and the filtrate was concentrated. The residue was purified by prep LC using 30% EtOAC/hexane to furnish 11.74 g (83% yield for three steps) of the title compound as a thick oil.

$^1$H NMR (CDCl$_3$, ppm ranges are given because of amide rotomers and line broadening) δ 1.38 (s, 9H), 2.69 & 2.75 (2s, 3H), 2.6–3.65 (m, 5H), 6.95–7.4 (m, 3H), 9.67 (s, 1H).

EXAMPLE 38

1'-[3-(S)-(3,4-dichlorophenyl)-4-(t-butoxycarbonyl (methylamino))butyl]-spiro(1H-indene-1,4'-piperidine).

To a solution of 3.46 g (10 mmol) of 3-(S)-(3,4-dichlorophenyl)-4-(t-butoxycarbonyl-methylamino)butanal (Example 1) in 20 mL of methanol were added 3.11 g (14 mmol) of spiro(1H-indene-1,4'-piperidine) hydrochloride and 3 g of powdered 4 Å molecular sieves. After 15 min a solution of 2.52 g (40 mmol) of NaCNBH3 in 30 mL of THF was dropwise added. Some gas evolution was observed. After stirring the reaction overnight, the mixture was filtered through a pad of celite, the reaction flask and the pad were rinsed with methanol. The filtrate was concentrated to approximately 10 ml and the residue was partitioned between saturated NaHCO3 and Et2O:EtOAC. The organic layer was washed with water, brine and dried over NA2SO4. The filtrate was concentrated and the residue was chromatographed on a flash column using a gradient of 49:49:2 to 98:0:2 EtOAc:Hexane:triethylamine to furnish 4.05 g (79%) of the title compound as a foam.

$^1$H NMR (CDCl3, ppm ranges are given because of amide rotomers and line broadening) δ 1.37 (s, 9H), 1.5–3.6 (m, 15H), 2.63 & 2.73 (2 s, 3H), 6.70 (d, 1 H, J=6 Hz), 6.77 (d, 1 H, J=6 Hz), 6.95–7.4 (m, 7H).

EXAMPLE 39

1'-[3-(S)-(3,4-dichlorophenyl)-4-(N-(3,5-dichloro) benzoyl-(methylamino))butyl]-spiro(1H-indene-1,4'-piperidine)

Step A: 1'[3-((S)-(3,4-dichlorophenyl))-4-(methylamino) butyl]-spir[1-H-indene-1,4'-piperidine].

Cold trifluoroacetic acid (TFA, 5 mL) and 0.2 mL of anisole were added to 0.565 g (1.1 mmol) of 1'[3-(S)-(3,4-dichlorophenyl)-4-(t-butoxycarbonyl(methylamino))butyl]-spiro(1H-indene-1,4'-piperidine) and the mixture was stirred in ice bath until all the foam dissolved. After stirring the resulting solution at room temperature for 30 min, it was concentrated in vacuo. The residue was partitioned between dilute NaOH (ca. 0.5N) and CH2Cl2 and the layers were separated. The organic layer was washed with brine, dried over Na2SO4 and concentrated to give 0.523 g of foam which was used in the next step without purification.

$^1$H NMR (CDCl3, ppm ranges are given because of amide rotomers and line broadening) δ 1.7–2.7 (m, 10H), 2.64 (s, 3H), 2.88 (s, 3H), 2.9–3.4 (m, 5H), 3.70 (s, 2H), 6.8–7.4 (m, 7H).

Step B: 1'[3-(S)-(3,4-dichlorophenyl)-4-(N-(3,5-dichloro) benzoyl-(methylamino))butyl]-spiro(1H-indene-1,4'-piperidine)

A solution of 0.105 g (0.55 mmol) of 3,5-dichlorobenzoic acid in 1 mL of CH2Cl2 and 2 drops of DMF was treated with 54 μL of oxalyl chloride. (Gas evolution!) After 20 min the solution was concentrated in vacuo and the residue was mixed with 0.152 g (0.36 mmol) of 1'[3-((S)-(3,4-dichlorophenyl))-4-(methylamino)butyl]-spiro[1H-indene-1,4'-piperidine obtained from step A, and 0.1 mL (0.71 mmol) of Et3N in 2 mL of CH2Cl2. After 1 h the reaction mixture was diluted with CH2Cl2 and washed with saturated NaHCO3, water, and brine. The CH2Cl2 solution was dried over Na2SO4, filtered and concentrated. Purification of the residue by prep TLC using 10% methanol-EtOAc afforded 0.18 g (84% yield) of the title compound as a foam.

$^1$H NMR (CDCl3, ppm ranges are given because of amide rotomers and line broadening) δ 1.6–2.4 (m, 10H), 2.27 (s, 6H), 2.6–3.9 (m, 10H), 2.86 (s, 3H), 6.6–7.5 (m, 10H).

Mass Spectrum (FAB) 589($^{37}$Cl+$^{35}$Cl isotope), 587($^{35}$Cl+$^{35}$Cl isotope).

The following compounds were prepared by substituting the required acid chloride for 3,5-dichlorobenzoyl chloride in step B.

EXAMPLE 40

1'-[3-(S)-(3,4-dichlorophenyl)-4-(N-(3-chloro) benzoyl-(methylamino))butyl]-spiro(1H-indene-1,4'-piperidine)

Mass Spectrum (FAB) 555($^{37}$Cl+$^{35}$Cl isotope), 553($^{35}$Cl+$^{35}$Cl isotope).

EXAMPLE 41

1'-[3-(S)-(3,4-dichlorophenyl)-4-(N-(3-trifluoromethyl)benzoyl-(methylamino))butyl]-spiro (1H-indene-1,4'-piperidine)

Mass Spectrum (FAB) 589($^{37}$Cl+$^{35}$Cl isotope), 587($^{35}$Cl+$^{35}$Cl isotope).

EXAMPLE 42

1'-[3-(S)-(3,4-dichlorophenyl)-4-(N-(3-isopropyloxy)benzoyl-(methylamino))butyl]-spiro (1H-indene-1,4'-piperidine)

Mass Spectrum (FAB) 579($^{37}$Cl+$^{35}$Cl isotope), 577($^{35}$Cl+$^{35}$Cl isotope).

EXAMPLE 43

1'-[3-(S)-(3,4-dichlorophenyl)-4-(N-(3-isopropyloxy)phenylacetyl-(methylamino))butyl]-spiro(1H-indene-1,4'-piperidine)

Mass Spectrum (FAB) 593($^{37}$Cl+$^{35}$Cl isotope), 591($^{35}$Cl+$^{35}$Cl isotope).

EXAMPLE 44

1'-[3(S)-(3,4-dichlorophenyl)-4-(N-(4-t-butyl) benzoyl-(methylamino))butyl]-spiro(1H-indene-1,4'-piperidine)

Mass Spectrum (FAB) 577($^{37}$Cl+$^{35}$Cl isotope), 575($^{35}$Cl+$^{35}$Cl isotope).

EXAMPLE 45

1'-[3-(S)-(3,4-dichlorophenyl)-4-(N-(2-phenyl) benzoyl-(methylamino))butyl]-spiro (1H-indene-1, 4'-piperidine)

Mass Spectrum (FAB) 597($^{37}$Cl+$^{35}$Cl isotope), 595($^{35}$Cl+$^{35}$Cl isotope).

EXAMPLE 46

1'-[3-(S)-(3,4-dichlorophenyl)-4-(N-(1-naphthoyl)-(methylamino))butyl]-spiro(1H-indene-1,4'-piperidine)

Mass Spectrum (FAB) 571($^{37}$Cl+$^{35}$Cl isotope), 569($^{35}$Cl+$^{35}$Cl isotope).

EXAMPLE 47

1'-[3-(S)-(3,4-dichlorophenyl)-4-(N-(2-naphthoyl (methylamino))butyl]-spiro(1H-indene-1,4'-piperidine)

Mass Spectrum (FAB) 571($^{37}$Cl+$^{35}$Cl isotope), 569($^{35}$Cl+$^{35}$Cl isotope).

EXAMPLE 48

1'-[3-(S)-(3,4-dichlorophenyl)-4-(N-(2-methyl) benzoyl-(methylamino))butyl]-spiro(1H-indene-1,4'-piperidine)

Mass Spectrum (FAB) 535 ($^{37}$Cl+$^{35}$Cl isotope, M+1), 533 ($^{35}$Cl+$^{35}$Cl isotope M+1).

EXAMPLE 49

1'-[3-(S)-(3,4-dichlorophenyl)-4-(N-(3-methyl) benzoyl-(methylamino))butyl]-spiro(1H-indene-1,4'-piperidine)

Mass Spectrum (FAB) 535 ($^{37}$Cl+$^{35}$Cl isotope, M+1), 533($^{35}$Cl+$^{35}$Cl isotope, M+1).

EXAMPLE 50

1'-[3-(S)-(3,4-dichlorophenyl)-4-(N-(3-methyl) benzoyl-(methylamino))butyl]-spiro(1H-indene-1,4'-piperidine).

Mass Spectrum (FAB) 535 ($^{37}$Cl+$^{35}$Cl isotope), 533 ($^{35}$Cl+$^{35}$Cl isotope, M+1).

EXAMPLE 51

1'-[3-(S)-(3,4-dichlorophenyl)-4-(N-(3,5-dimethyl) benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 52

1'-[3-(S)-(3,4-dichlorophenyl)-4-(N-(2,3-dimethyl) benzoyl-(methylamino))butyl]-spiro (1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 53

1'-[3-(S)-(3,4-dichlorophenyl)-4-(N-(3,4-dimethyl) benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 54

1'-[3-(S)-(3,4-dichlorophenyl)-4-(N-(2,5-dimethyl) benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 55

1'-[3-(S)-(3,4-dichlorophenyl)-4-(N-(2,4-dimethyl) benzoyl-(methylamino))butyl]-spiro(1H-indene-1,4'-piperidine)

Mass Spectrum (FAB) 549 ($^{37}$Cl+$^{35}$Cl isotope), 547 ($^{35}$Cl+$^{35}$Cl isotope).

EXAMPLE 56

1'-[3-(S)-(3,4-dichlorophenyl)-4-(trifluoroacetyl (methylamino))butyl]-spiro(1H-indene-1,4'-piperidine)

Mass Spectrum (FAB) 512($^{37}$Cl+$^{35}$Cl isotope), 510($^{35}$Cl+$^{35}$Cl isotope).

EXAMPLE 57

1'-[3-(S)-(3,4-dichlorophenyl)-4-(t-butylcarbonyl (methylamino))butyl]-spiro(1H-indene-1,4'-piperidine)

Mass Spectrum (FAB) 501 ($^{37}$Cl+$^{35}$Cl isotope), 499 ($^{35}$Cl+$^{35}$Cl isotope).

EXAMPLE 58

1'-[3-(S)-(3,4-dichlorophenyl)-4-(1,4'-adamentanecarbonyl(methylamino))butyl]-spiro(1H-indene-1,4'-piperidine)

Mass Spectrum (FAB) 579 ($^{37}$Cl+$^{35}$Cl isotope), 577 ($^{35}$Cl+$^{35}$Cl isotope).

EXAMPLE 59

1'-[3-(S)-(3,4-dichlorophenyl)-4-(cyclohexanecarbonyl(methylamino))butyl]-spiro (1H-indene-1,4'-piperidine)

Mass Spectrum (FAB) 527 ($^{37}$Cl+$^{35}$Cl isotope), 525 ($^{35}$Cl+$^{35}$Cl isotope).

EXAMPLE 60

1'-[3-(S)-(3,4-dichlorophenyl)-4-(N-(3-methyl) benzoyl-(methylamino))butyl]-spiro[indane-1,4'-piperidine]

A mixture of 50 mg (0.093 mmol) of 1'[3-(S)-(3,4-dichlorophenyl)-4-(N-(3-methyl)benzoyl-(methylamino)) butyl]-spiro(1H-indene-1,4'-piperidine). (Example 50) and 10 mg of 10% palladium on carbon catalyst in 1 mL of ethanol was hydrogenated on a Parr apparatus. After 30 min the catalyst was filtered on a pad of celite and the filtered solids were washed with EtOAc. The filtrate was concentrated in vacuo and the residue was purified by prep TLC using 2% Et3N/EtOAc to isolate 35 mg of the title compound as a foam.

(Mass Spectrum (FAB) 537 ($^{37}$Cl+$^{35}$Cl isotope), 535 ($^{35}$Cl+$^{35}$Cl isotope).

EXAMPLE 61

1'-[3-(S)-(3,4-dichlorophenyl)-4-(N-(3,5-dimethyl) benzoyl-(methylamino))butyl]-spiro[indane-1,4'-piperidine]

The title compound was prepared from 1'[3-(S)-(3,4-dichlorophenyl)-4-(N-(3,5-dimethyl)benzoyl-(methylamino))butyl]-spiro(1H-indene-1,4'-piperidine). (Example 51) by following the procedure of example 24.

Mass Spectrum (FAB) 551 ($^{37}$Cl+$^{35}$Cl isotope), 549 ($^{35}$Cl+$^{35}$Cl isotope).

EXAMPLE 62

1'-[3-(S)-(3,4-dichlorophenyl)-4-(N-(3,5-bistrifluoromethyl)benzoyl-(methylamino))butyl]-spiro[(3-indanone)-1,4'-piperidine]

A solution of 98 mg (0.2 mmol) of 3-(S)-(3,4-dichlorophenyl)-4-((3,5-bistrifluoromethyl)benzoyl (methylamino))butanal and 44 mg (0.22 mmol) of spiro[(3-indanone)1,4'-piperidine in 2 mL of methanol was treated with 4 µL of HOAC and 0.2 g of powdered molecular sieves. After stirring for 1 h, 0.6 mL of 1M NaCNBH3 in THF was dropwise added and the resulting mixture was stirred for 30 min. The reaction was filtered through a pad of celite, the flask and the filtered solids were rinsed with EtOAc. The filtrate was diluted with EtOAc, washed with saturated NaHCO3, water, brine and dried over Na2SO4. The filtrate was concentrated and the residue was chromatographed on a prep TLC plate using 2% Et3N/EtOAc to furnish 51 mg (38% yield) of the title compound.

Mass Spectrum (FAB) ($^{37}Cl+^{35}Cl$ isotope), ($^{35}Cl+^{35}Cl$ isotope).

The following compounds were synthesized by an analogous procedure using the required aldehyde for the 3-(S)-(3,4-dichlorophenyl)-4-((3,5-bistrifluoromethyl)benzoyl (methylamino))butanal.

EXAMPLE 63

1'-[3-(S)-(3,4-dichlorophenyl)-4-(N-benzoyl-(methylamino))butyl]-spiro[(3-indanone)-1,4'-piperidine]

Mass Spectrum (FAB) 537 ($^{37}Cl+^{35}Cl$ isotope), 535 ($^{35}Cl+^{35}Cl$ isotope).

EXAMPLE 64

1'-[3-(S)-(3,4-dichlorophenyl)-4-(N-(3,5-dimethyl) benzoyl-(methylamino))butyl]-spiro[(3-indanone)-1,4'-piperidine]

Mass Spectrum (FAB) 565 ($^{37}Cl+^{35}Cl$ isotope), 563 ($^{35}Cl+^{35}Cl$ isotope).

EXAMPLE 65

1'-[3-(S)-(3,4-dichlorophenyl)-4-(t-butoxycarbonyl (methylamino))butyl]-spiro[(3-indanone)-1,4'-piperidine].

Mass Spectrum (FAB) 533 ($^{37}Cl+^{35}Cl$ isotope), 531 ($^{35}Cl+^{35}Cl$ isotope).

EXAMPLE 66

1'-[3-(S)-(3,4-dichlorophenyl)-4-(N-(3,5-dichloro) benzoyl-(methylamino))butyl]-spiro[(3-indanone)-1,4'-piperidine]

Step A: 1'[3-(S)-(3,4-dichlorophenyl)-4-(methylamino) butyl]-spiro[(3-indanone)-1,4'-piperidine]

Treatment of 0.58 g (1.09 mmol) of 1'[3-(S)-(3,4-dichlorophenyl)-4-(t-butoxycarbonyl(methylamino))butyl]-spiro[(3-indanone)-1,4'-piperidine] with TFA and anisole according to the procedure of example 39, step A furnished 0.56 g of the title compound which was sufficiently pure for use in step B.

Step B: 1'[3-(S)-(3,4-dichlorophenyl)-4-(N-(3,5-dichloro) benzoyl-(methylamino))butyl]-spiro[(3-indanone)-1,4'-piperidine]

Reaction of 95 mg (0.22 mmol) of 1'[3-(S)-(3,4-dichlorophenyl)-4-(methylamino)butyl]-spiro[(3-indanone)-1,4'-piperidine] from step A above, with 3,5-dichlorobenzoyl chloride by the procedure of example 39 step B gave the title compound which was purified by prep TLC.

Mass Spectrum (FAB) 607 ($^{37}Cl+^{35}Cl$ isotope), 605 ($^{35}Cl+^{35}Cl$ isotope).

The following compounds were prepared by substituting the required acid chloride for 3,5-dichlorobenzoyl chloride in step B.

EXAMPLE 67

1'-[3-(S)-(3,4-dichlorophenyl)-4-(N-(3-chloro-5-methyl)benzoyl-(methylamino))butyl]-spiro[(3-indanone)-1,4'-piperidine]

Mass Spectrum (FAB) 584 ($^{37}Cl+^{35}Cl$ isotope), 582 ($^{35}Cl+^{35}Cl$ isotope).

EXAMPLE 68

1'-[3-(S)-(3,4-dichlorophenyl)-4-(N-(3-fluoro-5-methyl)benzoyl-(methylamino))butyl]-spiro[(3-indanone)-1,4'-piperidine]

Mass Spectrum (FAB) 622 ($^{37}Cl+^{35}Cl$ isotope), 620 ($^{35}Cl+^{35}Cl$ isotope).

EXAMPLE 69

1'-[3-(S)-(3,4-dichlorophenyl)-4-(1-naphthoyl (methylamino))butyl]-spiro[(3-indanone)-1,4'-piperidine]

Mass Spectrum (FAB) 587 ($^{37}Cl+^{35}Cl$ isotope), 585 ($^{35}Cl+^{35}Cl$ isotope).

EXAMPLE 70

1'-[3-(S)-(3,4-dichlorophenyl)-4-(N-(3,5-dimethyl) benzoyl-(methylamino))butyl]-spiro[(3-hydroxy) indane)-1,4'-piperidine]

A solution of 0.384 g (0.68 mmol) of 1'[3-(S)-(3,4-dichlorophenyl)-4-((3,5-dimethyl)benzoyl(methylamino)) butyl]-spiro[(3-indanone)-1,4'-piperidine] (example 64) in 3 mL of methanol was treated with 13 mg (0.34 mmol) of NaBH4. Two additional 13 mg (0.34 mmol) portions of NaBH4 were added after 45 min intervals and the mixture was stirred another 45 min. The excess NaBH4 was destroyed by adding few drops of 10% HCl, diluted with water and the mixture was extracted with EtOAc. The organic phase was washed with water, brine and dried with Na2SO4. The residue after concentration of the filtrate was chromatographed on a flash column to isolate 0.313 g (81% yield) of the title compound.

Mass Spectrum (FAB) 567 ($^{37}Cl+^{35}Cl$ isotope), 565 ($^{35}Cl+^{35}Cl$ isotope).

EXAMPLE 71

1'-[3-(S)-(3,4-dichlorophenyl)-4-(N-(3,5-dimethyl) benzoyl-(methylamino))butyl]-spiro[(3-acetyloxy) indane)-1,4'-piperidine]

The title compound was obtained by acylation of 1'[3-(S)-(3,4-dichlorophenyl)-4-((3,5-dimethyl)benzoyl (methylamino))butyl]-spiro[(3-hydroxy)indane)-1,4'-piperidine] (example 70) with acetyl chloride and Et3N in CH2Cl2.

Mass Spectrum (FAB) 609 ($^{37}Cl+^{35}Cl$ isotope), 607 ($^{35}Cl+^{35}Cl$ isotope).

EXAMPLE 72

1'-[3-(S)-(3,4-dichlorophenyl)-4-(N-(3,5-dimethyl) benzoyl-(methylamino))butyl]-spiro[(3-methylamino-carbonyl-amino)indane-1,4'-piperidine]

Reductive amination of 3-(S)-(3,4-dichlorophenyl)-4-((3, 5-dimethyl)benzoyl(methylamino))butanal (75 mg, 0.2 mmol) and spiro[(3-methylamino-carbonyl-amino)indane-1,4'-piperidine] (53 mg, 0.22 mmol) by the procedure of example 62 furnished 70 mg (57% yield) of the title compound.

Mass Spectrum (FAB) 623 ($^{37}Cl+^{35}Cl$ isotope), 621 ($^{35}Cl+^{35}Cl$ isotope).

The following compounds were prepared by reacting the appropriate aldehyde with spiro[(3-ethoxycarbonyl)indane-1,4'-piperidine] according to the procedure of example 62.

EXAMPLE 73

1'-[3-(S)-(3,4-dichlorophenyl)-4-(N-(3,5-bistrifluoromethyl)benzoyl-(methylamino))butyl]-spiro[(3-ethoxycarbonyl)indane]-1,4'-piperidine]

Mass Spectrum (FAB) 729($^{37}Cl+^{35}Cl$ isotope), 727 ($^{35}Cl+^{35}Cl$ isotope).

EXAMPLE 74

1'-[3-(S)-(3,4-dichlorophenyl)-4-(benzoyl(methylamino))butyl]-spiro[(3-ethoxycarbonyl)indane)-1,4'-piperidine]

Mass Spectrum (FAB) 593($^{37}Cl+^{35}Cl$ isotope), 591($^{35}Cl+^{35}Cl$ isotope).

The compounds Exemplified in the above EXAMPLES have been found to displace radioactive ligand for the NK-1 receptor at a concentration range of 1 nM to 10 μM, for the NK-2 receptor, 0.1 nM to 5 μM, and for the NK-3 receptor, 10 nM to 10 μM.

What is claimed is:

1. A compound represented by the formula:

or a pharmaceutically acceptable salt thereof, wherein:
A is selected from the group consisting of:

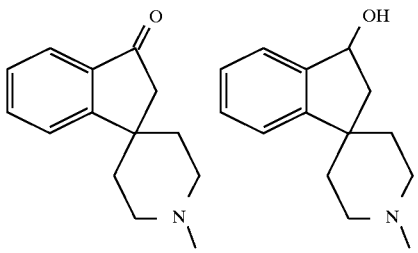

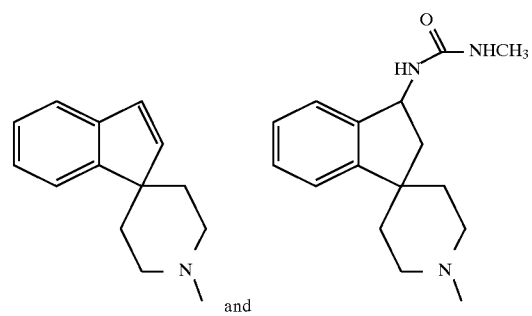

and $R_1$ is selected from a group consisting of:
linear or branched $C_{1-8}$ alkyl, linear or branched $C_{2-8}$ alkenyl, or linear or branched $C_{2-8}$ alkynyl,
said $C_{1-8}$ alkyl, $C_{2-8}$ alkenyl or $C_{2-8}$ alkynyl group being di, tri or tetra substituted with two to four members selected from the group consisting of:

(a) hydroxy,
(b) oxo,
(c) cyano,
(d) halogen selected from Br, Cl, I, and F,
(e) trifluoromethyl,
(f) phenyl or mono, di or trisubstituted phenyl, the substitutents being independently selected from:
  (1) phenyl,
  (2) hydroxy,
  (3) $C_{1-3}$alkyl,
  (4) cyano,
  (5) halogen,
  (6) trifluoromethyl,
  (7) —$NR_6COR_7$,
  (8) —$NR_6CO_2R_7$,
  (9) —$NR_6CONHR_7$,
  (10) —$NR_6S(O)_jR_7$, wherein j is 1 or 2,
  (11) —$CONR_6R_7$,
  (12) —$COR_6$,
  (13) —$CO_2R_6$,
  (14) —$OR_6$ and
  (15) —$S(O)_{k'}R_6$ wherein k' is 0, 1 or 2;
(g) —$NR_6R_7$,
(h) —$NR_6COR_7$,
(i) —$NR_6CO_2R_7$,
(j) —$NR_6CONHR_7$,
(k) —$NR_6S(O)_jR_7$,
(l) —$CONR_6R_7$,
(m) —$COR_6$,
(n) —$CO_2R_6$,
(o) —$OR_6$ and
(p) —$S(O)_{k'}R_6$, and $R_6$ and $R_7$ are independently selected from:
(a) hydrogen,
(b) $C_{1-6}$ alkyl, or mono or disubstituted $C_{1-6}$ alkyl, the substitutents independently selected from:
  (1) phenyl,
  (2) hydroxy,
  (3) oxo,
  (4) cyano,
  (5) halogen,
  (6) trifluoromethyl,
(c) phenyl or naphthyl or mono di or trisubstituted phenyl or naphthyl, the substitutents independently selected from
  (1) hydroxy,
  (2) $C_{1-3}$alkyl,
  (3) cyano,
  (4) halogen,
  (5) trifluoromethyl, and
(d) $C_{1-3}$ alkyloxy.

2. A compound represented by the formula:

or a pharmaceutically acceptable salt thereof, wherein:

A is selected from the group consisting of:

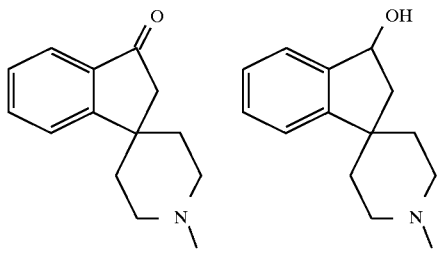

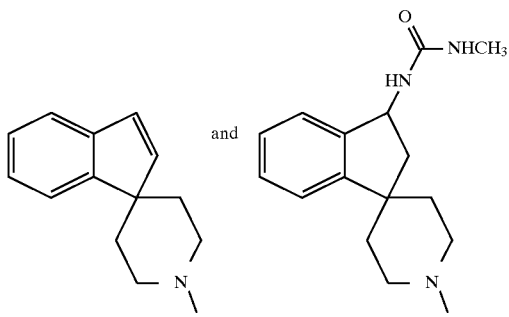

and $R_1$ is selected from a group consisting of:

$C_{2-6}$ linear or branched alkyl, di or trisubstituted, the substitutents independently selected from:
(a) phenyl or mono, di or trisubstituted phenyl, the substitutents independently selected from
  (1) phenyl,
  (2) hydroxy,
  (3) $C_{1-3}$alkyl,
  (4) cyano,
  (5) halogen,
  (6) trifluoromethyl,
(b) —$NR_6R_7$, wherein $R_6$ and $R_7$ are independently selected from:
  (1) hydrogen,
  (2) $C_{1-6}$ alkyl, unsubstituted or mono or disubstituted, the substitutents independently selected from hydroxy, halo, trifluoromethyl, $C_{1-3}$alkyl and phenyl;
  (3) phenyl or naphthyl, unsubstituted or mono or disubstituted, the substitutents independently selected from hydroxy, halo, trifluoromethyl, $C_{1-3}$alkyl and phenyl;
(c) —$NR_6COR_7$;
(d) —$NR_6CO_2R_7$,
(e) —$NR_6CONHR_7$.

3. A compound represented by the formula:

A—$R_1$ or a pharmaceutically acceptable salt thereof, wherein:

A is selected from the group consisting of:

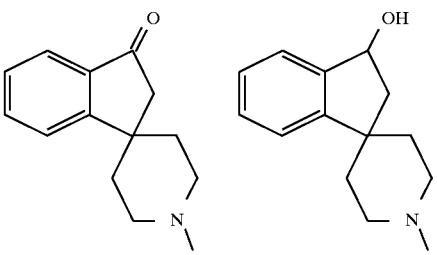

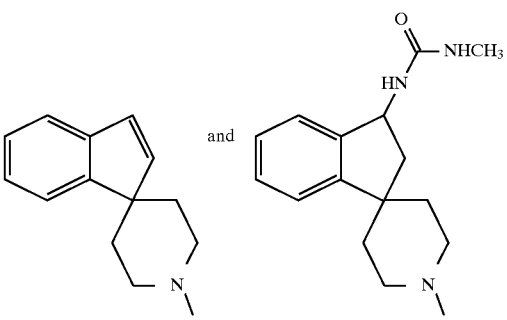

and $R_1$ is —$C_{2-4}$ alkyl—$C(R_8)H$—$C(R_9)HR_{10}$; wherein $R_{10}$ is H, $C_{1-4}$alkyl, or substituted phenyl wherein the substituent is H, $C_{1-3}$alkyl or halo;

$R_8$ is mono or disubstituted phenyl or naphthyl, wherein the substitutents are independently hydrogen, Cl, F, $CF_3$;

$R_9$ is —$NR_6COR_7$; wherein $R_6$ is hydrogen or $C_{1-3}$ alkyl; and $R_7$ is substituted phenyl, wherein the substitutent is hydrogen, Cl, F, $CF_3$, $C_{1-3}$alkyl.

4. A compound represented by the formula:

A—$R_1$ or a pharmaceutically acceptable salt thereof, wherein:

A is selected from the group consisting of:

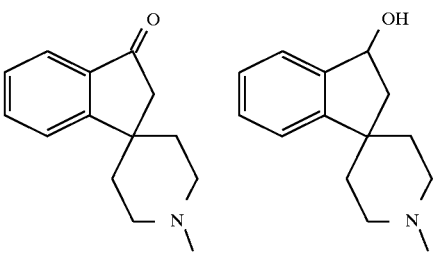

-continued

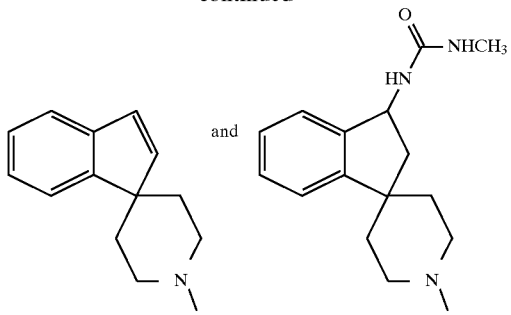

and R₁ is

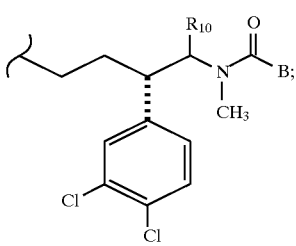

where B is phenyl or naphthyl or mono or disubstituted phenyl or naphthyl wherein the substitutent is $CF_3$, $CH_3$, Cl, Br, or F; and $R_{10}$ is H, $C_{1-3}$alkyl or phenyl.

5. A compound represented by the formula:

A—R₁ or a pharmaceutically acceptable salt thereof, wherein:

A is selected from the group consisting of:

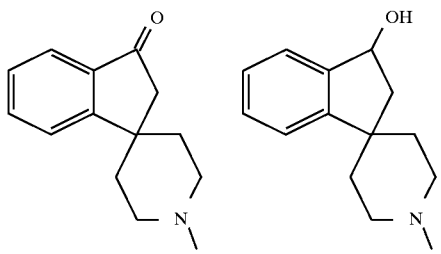

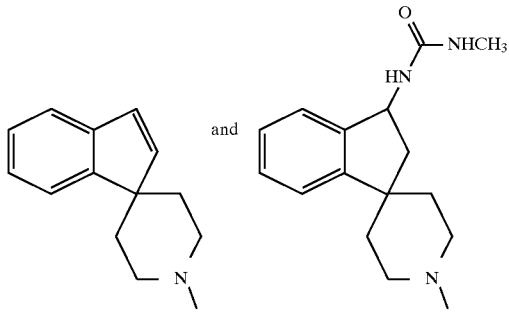

and R₁ is

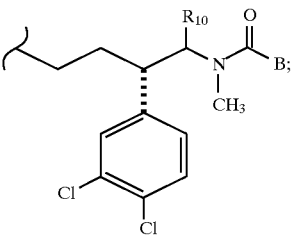

wherein B is (a) phenyl or naphthyl or mono di or trisubstituted phenyl or naphthyl wherein the substitutents are independently chloro, methyl, phenyl or $CF_3$;

(b) —$CH_2$phenyl or mono or disubstituted —$CH_2$phenyl wherein the substitutents are independently fluoro, chloro, methyl, phenyl or $CF_3$;

(c) pyridyl or mono di or trisubstituted pyridyl wherein the substitutents are independently chloro, methyl, phenyl or $CF_3$;

(d) thiophene or mono or disubstituted thiophene wherein the substitutents are independently chloro, methyl, phenyl or $CF_3$; and $R_{10}$ is H, $C_{1-3}$alkyl or phenyl.

6. A compound represented by the formula:

A—R₁ or a pharmaceutically acceptable salt thereof, wherein:

A is selected from the group consisting of:

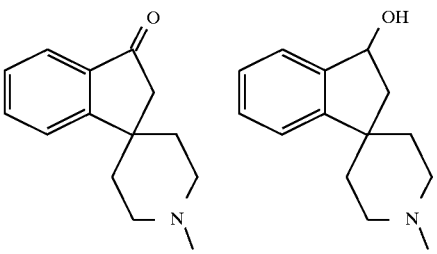

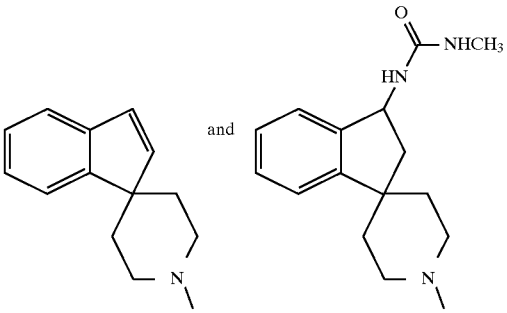

and R₁ is

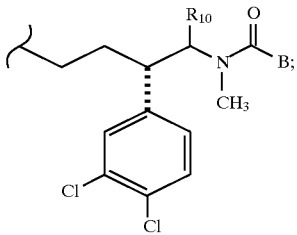

where B is phenyl or mono or disubstituted phenyl or naphthyl wherein the substituent is $CF_3$, $CH_3$, Cl, F, Br; and $R_{10}$ is H, $C_{1-3}$alkyl or phenyl.

7. A compound selected from the group consisting of:

1'-(3(S)-(3,4-Dichlorophenyl)-4-(N-methyl)benzamidobutyl)spiro(1H-indene-1,4'-piperidine), 1'-(3(S)-(3,4-Dichlorophenyl)-4-((N-methyl)-3,5-bis(trifluoromethyl)benzamidobutyl)spiro(1H-indene-1,4'-piperidine), 1'-(1-Oxo-(3S)-(3,4-dichlorophenyl)-4-(N-methyl)benzamidobutyl)spiro(1H-indene-1,4'-piperidine), 1'-((3S)-(3,4-Dichlorophenyl)-(4)-((N-methyl)benzamido)pentyl)spiro(1H-indene-1,4'-piperidine), 1'-((3S)-(3,4-Dichlorophenyl)-(4)-((N-methyl)benzamido)octyl)spiro(1H-indene-1,4'-piperidine), 1'-((4)-((3S)-(3,4-Dichlorophenyl)-1-(N-methyl)benzamido)octyl)spiro(1H-indene-1,4'-piperidine), 1'-((3S)-(3,4-Dichlorophenyl)-4-((N-methyl)benzenesulfonamidobutyl)spiro[1H-indene-1,4'-piperidine], 1'-((3S)-(3,4-Dichlorophenyl)-4-((N-methyl)furan-2-carboxamidobutyl)spiro[1H-indene-1,4'-piperidine], 1'-((3S)-(3,4-Dichlorophenyl)-4-((N-methyl)phenoxycarboxamidobutyl)spiro[1H-indene-1,4'-piperidine], 1'-((3S)-(3,4-Dichlorophenyl)-4-((N-methyl)phenylaminocarboxamidobutyl)spiro[1H-indene-1,4'-piperidine], 1'-((3S)-(3,4-Dichlorophenyl)-4-((N-methyl)pyridine-2-carboxamidobutyl)spiro[1H-indene-1,4'-piperidine], 1'-((3S)-(3,4-Dichlorophenyl)-4-((N-methyl)pyridine-3-carboxamidobutyl)spiro[1H-indene-1,4'-piperidine], 1'-((3S)-(3,4-Dichlorophenyl)-4-((N-methyl)pyridine-4-carboxamidobutyl)spiro[1H-indene-1,4'-piperidine], 1'-((3S)-(3,4-Dichlorophenyl)-4-((N-methyl)benzothiophene-2-carboxamidobutyl)spiro[1H-indene-1,4'-piperidine], 1'-((3S)-(3,4-Dichlorophenyl)-4-((N-methyl)thiophene-2-acetamidobutyl)spiro[1H-indene-1,4'-piperidine], 1'-((3S)-(3,4-Dichlorophenyl)-4-((N-methyl)thiophene-3-carboxamidobutyl)spiro[1H-indene-1,4'-piperidine], 1'-((3S)-(3,4-Dichlorophenyl)-4-((N-methyl)-(3-methylthiophene-2-carboxamido)butyl)spiro[1H-indene-1,4'-piperidine], 1'-((3S)-(3,4-Dichlorophenyl)-4-((N-methyl)-(5-methylthiophene-2-carboxamido)butyl)spiro[1H-indene-1,4'-piperidine], 1'-((3S)-(3,4-Dichlorophenyl)-4-((N-methyl)-(5-chlorothiophene-2-carboxamido)butyl)spiro[1H-indene-1,4'-piperidine], 1'-((3S)-(3,4-Dichlorophenyl)-4-((N-methyl)-(2,3-dibromothiophene-5-carboxamido)butyl)spiro[1H-indene-1,4'-piperidine], 1'-[3-(S)-(3,4-dichlorophenyl)-4-(t-butoxycarbonyl(methylamino))butyl]-spiro(1H-indene-1,4'-piperidine), 1'-[3-(S)-(3,4-dichlorophenyl)-4-(N-(3,5-dichloro)benzoyl-(methylamino))butyl]-spiro(1H-indene-1,4'-piperidine), 1'-[3-(S)-(3,4-dichlorophenyl)-4-(N-(3-chloro)benzoyl-(methylamino))butyl]-spiro(1H-indene-1,4'-piperidine), 1'-[3-(S)-(3,4-dichlorophenyl)-4-(N-(3-trifluoromethyl)benzoyl-(methylamino))butyl]-spiro(1H-indene-1,4'-piperidine), 1'-[3-(S)-(3,4-dichlorophenyl)-4-(N-(3-isopropyloxy)benzoyl-(methylamino))butyl]-spiro(1H-indene-1,4'-piperidine), 1'-[3-(S)-(3,4-dichlorophenyl)-4-(N-(3-isopropyloxy)phenylacetyl-(methylamino))butyl]-spiro(1H-indene-1,4'-piperidine), 1'-[3-(S)-(3,4-dichlorophenyl)-4-(N-(4-t-butyl)benzoyl-(methylamino))butyl]-spiro(1H-indene-1,4'-piperidine, 1'-[3-(S)-(3,4-dichlorophenyl)-4-(N-(2-phenyl)benzoyl-(methylamino))butyl]-spiro(1H-indene-1,4'-piperidine), 1'-[3-(S)-(3,4-dichlorophenyl)-4-(N-(1-naphthoyl(methylamino))butyl]-spiro(1H-indene-1,4'-piperidine), 1'-[3-(S)-(3,4-dichlorophenyl)-4-(N-(2-naphthoyl(methylamino))butyl]-spiro(1H-indene-1,4'-piperidine), 1'-[3-(S)-(3,4-dichlorophenyl)-4-(N-(2-methyl)benzoyl-(methylamino))butyl]-spiro(1H-indene-1,4'-piperidine), 1'-[3-(S)-(3,4-dichlorophenyl)-4-(N-(4-methyl)benzoyl-(methylamino))butyl]-spiro(1H-indene-1,4'-piperidine), 1'-[3-(S)-(3,4-dichlorophenyl)-4-(N-(3-methyl)benzoyl-(methylamino))butyl]-spiro(1H-indene-1,4'-piperidine), 1'-[3-(S)-(3,4-dichlorophenyl)-4-(N-(3,5-dimethyl)benzoyl-(methylamino))butyl]-spiro(1H-indene-1,4'-piperidine), 1'-[3-(S)-(3,4-dichlorophenyl)-4-(N-(2,3-dimethyl)benzoyl-(methylamino))butyl]-spiro(1H-indene-1,4'-piperidine), 1'-[3-(S)-(3,4-dichlorophenyl)-4-(N-(3,4-dimethyl)benzoyl-(methylamino))butyl]-spiro(1H-indene-1,4'-piperidine), 1'-[3-(S)-(3,4-dichlorophenyl)-4-(N-(2,5-dimethyl)benzoyl-(methylamino))butyl]-spiro(1H-indene-1,4'-piperidine), 1'-[3-(S)-(3,4-dichlorophenyl)-4-(N-(2,4-dimethyl)benzoyl-(methylamino))butyl]-spiro(1H-indene-1,4'-piperidine), 1'-[3-(S)-(3,4-dichlorophenyl)-4-(trifluoroacetyl(methylamino))butyl]-spiro(1H-indene-1,4'-piperidine), 1'-[3-(S)-(3,4-dichlorophenyl)-4-(t-butylcarbonyl(methylamino))butyl]-spiro(1H-indene-1,4'-piperidine), 1'-[3-(S)-(3,4-dichlorophenyl)-4-(1-adamentanecarbonyl(methylamino))butyl]-spiro(1H-indene-1,4'-piperidine), 1'-[3-(S)-(3,4-dichlorophenyl)-4-(cyclohexanecarbonyl(methylamino))butyl]-spiro( 1H-indene-1,4'-piperidine), 1'-[3-(S)-(3,4-dichlorophenyl)-4-(N-(3,5-bistrifluoromethyl)benzoyl-(methylamino))butyl]-spiro[(3-indanone)-1,4'-piperidine], 1'-[3-(S)-(3,4-dichlorophenyl)-4-(N-benzoyl-(methylamino))butyl]-spiro[(3-indanone)-1,4'-piperidine], 1'-[3-(S)-(3,4-dichlorophenyl)-4-(N-(3,5-dimethyl)benzoyl-(methylamino))butyl]-spiro[(3-indanone)-1,4'-piperidine], 1'-[3-(S)-(3,4-dichlorophenyl)-4-(t-butoxycarbonyl(methylamino))butyl]-spiro[(3-indanone)-1,4'-piperidine], 1'-[3-(S)-(3,4-dichlorophenyl)-4-(N-(3,5-dichloro)benzoyl-(methylamino))butyl]-spiro[(3-indanone)-1,4'-piperidine], 1'-[3-(S)-(3,4-dichlorophenyl)-4-(N-(3-chloro-5-methyl)benzoyl-(methylamino))butyl]-spiro[(3-indanone)-1,4'-piperidine], 1'-[3-(S)-(3,4-dichlorophenyl)-4-(N-(3-fluoro-5-methyl)benzoyl-(methylamino))butyl]-spiro[(3-indanone)-1,4'-piperidine], 1'-[3-(S)-(3,4-dichlorophenyl)-4-(1-naphthoyl(methylamino))butyl]-spiro[(3-indanone)-1,4'-piperidine], 1'-[3-(S)-(3,4-dichlorophenyl)-4-(N-(3,5-dimethyl)benzoyl-(methylamino))butyl]-spiro[(3-hydroxy)indane)-1,4'-piperidine], and 1'-[3-(S)-(3,4-dichlorophenyl)-4-(N-(3,5-dimethyl)benzoyl-(methylamino))butyl]-spiro[(3-methylamino-carbonyl-amino)indane-1,4'-piperidine].

8. A compound according to claim 1 wherein $R_1$ is selected from a group consisting of:

$C_1$, $C_2$, $C_3$, $C_4$, $C_5$ or $C_6$ linear or branched alkyl, di tri or tetra substituted, the substitutents independently selected from:
(a) oxo,
(b) phenyl or mono, di or trisubstituted phenyl, the substitutents independently selected from
  (1) phenyl,
  (2) hydroxy,
  (3) $C_{1-3}$alkyl,
  (4) cyano,
  (5) halogen,
  (6) trifluoromethyl,
  (7) —$NR_6COR_7$, wherein $R_6$ and $R_7$ are independently selected from:
(a) hydrogen,
(b) $C_{1-6}$ alkyl, or mono or disubstituted $C_{1-6}$ alkyl, the substitutents independently selected from
  (1) phenyl,
  (2) hydroxy,
  (3) oxo,
  (4) cyano,
  (5) halogen,
  (6) trifluoromethyl,
(c) phenyl or naphthyl or mono di or trisubstituted phenyl or naphthyl, the substitutents independently selected from
  (1) hydroxy,
  (2) $C_{1-3}$alkyl,
  (3) cyano,
  (4) halogen,
  (5) trifluoromethyl, or
(d) $C_{1-3}$alkyloxy,
  (8) —$NR_6CO_2R_7$,
  (9) —$NR_6CONHR_7$,
  (10) —$NR_6S(O)_jR_7$, wherein j is 1 or 2,
  (11) —$CONR_6R_7$,
  (12) —$COR_6$,
  (13) —$CO_2R_6$,
  (14) —$OR_6$ and
  (15) —$S(O)_kR_6$,
(c) —$NR_6R_7$,
(d) —$NR_6COR_7$,
(e) —$NR_6CO_2R_7$,
(f) —$NR_6CONHR_7$,
(g) —$CONR_6R_7$,
(h) —$CO_2R_6$ and
(i) —$OR_6$.

9. A compound which is:
1'-[(3-(S)-(3,4-Dichlorophenyl)-4-(N-(3-fluoro-5-methyl)benzoyl-(methylamino)butyl]-spiro[(3-indanone)-1,4'-piperidine] or a pharmaceutically acceptable salt thereof.

10. A pharmaceutical composition for antagonizing the effect of substance P in a patient in need of such treatment comprising a pharmaceutically acceptable carrier and a non-toxic therapeutically effective amount of the compound of claim 9.

11. A pharmaceutical composition for antagonizing the effect of substance P in a patient in need of such treatment comprising a pharmaceutically acceptable carrier and a non-toxic therapeutically effective amount of the compound of claim 1.

12. A pharmaceutical composition for the antagonizing the effect of neurokinin A, in a patient in need of such treatment comprising a pharmaceutically acceptable carrier and a non-toxic therapeutically effective amount of the compound of claim 1.

13. A method for antagonizing the effect of substance P in a patient in need of such treatment which comprises the administration to the patient of a non-toxic therapeutically effective amount of the compound according to claim 1.

14. A method for antagonizing the effect of neurokinin A in a patient in need of such antagonizing which comprises the administration to the patient of a non-toxic therapeutically effective amount of the compound according to claim 1.

15. A method of treating or reducing the risk of developing asthma in a patient in need thereof which comprises the administration to the patient of a non-toxic therapeutically effective amount of the compound of claim 1.

16. A method of treating or reducing the risk of developing emesis in a patient in need thereof which comprises the administration to the patient of a non-toxic therapeutically effective amount of the compound of claim 1.

* * * * *